(12) United States Patent
Shimmick

(10) Patent No.: US 7,133,137 B2
(45) Date of Patent: Nov. 7, 2006

(54) INTEGRATED SCANNING AND OCULAR TOMOGRAPHY SYSTEM AND METHOD

(75) Inventor: John K. Shimmick, Belmont, CA (US)

(73) Assignee: Visx, Incorporated, Santa Clara, CA (US)

( * ) Notice: Subject to any disclaimer, the term of this patent is extended or adjusted under 35 U.S.C. 154(b) by 314 days.

(21) Appl. No.: 10/601,119

(22) Filed: Jun. 19, 2003

(65) Prior Publication Data

US 2004/0021874 A1 Feb. 5, 2004

Related U.S. Application Data

(60) Provisional application No. 60/392,330, filed on Jun. 27, 2002.

(51) Int. Cl.
*G01B 9/02* (2006.01)
*G01B 11/02* (2006.01)
*A61B 18/18* (2006.01)

(52) U.S. Cl. ............... 356/497; 356/479; 356/503
(58) Field of Classification Search ............ 356/479, 356/496, 497, 498, 503, 504, 505
See application file for complete search history.

(56) References Cited

U.S. PATENT DOCUMENTS

| | | |
|---|---|---|
| 3,735,036 A | 5/1973 | Macovksi |
| 4,665,913 A | 5/1987 | L'Esperance, Jr. |
| 4,884,697 A | 12/1989 | Takacs et al. |
| 4,984,883 A | 1/1991 | Winocur |
| 5,062,702 A | 11/1991 | Bille |
| 5,116,115 A | 5/1992 | Lange et al. |
| 5,144,630 A | 9/1992 | Lin |
| 5,260,761 A | 11/1993 | Barker |
| 5,317,389 A | 5/1994 | Hochberg et al. |
| 5,321,501 A * | 6/1994 | Swanson et al. ............ 356/479 |
| 5,349,440 A | 9/1994 | DeGroot |
| 5,406,342 A | 4/1995 | Jongsma |
| 5,459,570 A * | 10/1995 | Swanson et al. ............ 356/479 |

(Continued)

FOREIGN PATENT DOCUMENTS

WO  WO 9901716  1/1999

OTHER PUBLICATIONS

Borsuztky et al., "Tunable UV Radiation at Short Wavelengths (188-240nm) Generated by Sum Frequency Mixing in Lithium Borate," Appl. Phys., 852:380-384 (1991).

(Continued)

*Primary Examiner*—Layla G. Lauchman
*Assistant Examiner*—Michael A. Lyons
(74) *Attorney, Agent, or Firm*—Townsend & Townsend & Crew LLP; John K. Shimmick

(57) ABSTRACT

Systems and methods of the present invention measure at least one reflecting surface of an object disposed along an optical path. In some embodiments a measured optical interference signal for each of at least three wavelengths of reflected light may be used to determine a modulation of frequency components of a Fourier series. Frequency components of a Fourier series may be transformed to spatial components that describe intensities and positions of light reflected along an optical path.

Systems and methods of the present invention permit rapid measuring and may monitor corneal thickness during surgery. The invention may do so by integrating an ablation device and a measurement apparatus into a single system. An integrated scanning and monitoring system may include an ablative light source producing an ablative beam and a measurement light source producing a measurement beam.

27 Claims, 12 Drawing Sheets

U.S. PATENT DOCUMENTS

| | | |
|---|---|---|
| 5,521,657 A | 5/1996 | Klopotek |
| 5,610,716 A * | 3/1997 | Sorin et al. .................. 356/479 |
| 5,646,791 A | 7/1997 | Glockler |
| 5,683,379 A | 11/1997 | Hohla |
| 5,713,892 A | 2/1998 | Shimmick |
| 5,742,626 A | 4/1998 | Mead et al. |
| 5,909,270 A | 6/1999 | Moser et al. |
| 5,912,775 A | 6/1999 | Glockler |
| 5,912,779 A | 6/1999 | Llewellyn et al. |
| 6,203,539 B1 | 3/2001 | Shimmick et al. |
| 6,280,435 B1 | 8/2001 | Odrich et al. |
| 6,319,247 B1 | 11/2001 | Hofer et al. |
| 6,331,177 B1 | 12/2001 | Munnerlyn et al. |
| 6,448,094 B1 * | 9/2002 | Yamazawa et al. ............ 438/9 |
| 6,451,009 B1 | 9/2002 | Dasilva et al. |
| 6,454,761 B1 | 9/2002 | Freedman |
| 6,501,551 B1 | 12/2002 | Tearney et al. |
| 6,815,228 B1 * | 11/2004 | Usui et al. .................... 438/14 |
| 6,882,431 B1 * | 4/2005 | Teich et al. ................. 356/497 |
| 2003/0025913 A1 | 2/2003 | Izatt et al. |

OTHER PUBLICATIONS

Bohnke et al., "Real-time pachymetry during photorefractive keratectomy using low-coherence reflectometry" *Journal of Biomedical Optics* 6(4) (Oct. 2001), pp. 412-417.

\* cited by examiner

| | | | | | | |
|---|---|---|---|---|---|---|
| wavelength (m) | 8.00E-07 | | | | | |
| velocity m/s | 1 | | | | | |
| cycles/m | 1.25E+06 | | | | | |
| cycles/s | 1.25E+06 | | | | | |

| Etalon Oscillations (interger) | wavelength (meters) | delta wavelength (nm) | Doppler Frequency (Hz) | Delta Doppler (Hz) | Spatial Frequency (cycles/mm) | Delta Spatial Frequency (cycles/mm) |
|---|---|---|---|---|---|---|
| 2480 | 8.06452E-07 | 0.325051033 | 1.2400E+06 | -5.00E+02 | 1240 | -0.5 |
| 2481 | 8.06127E-07 | 0.324789106 | 1.2405E+06 | -5.00E+02 | 1240.5 | -0.5 |
| 2482 | 8.05802E-07 | 0.324527496 | 1.2410E+06 | -5.00E+02 | 1241 | -0.5 |
| 2483 | 8.05477E-07 | 0.324266202 | 1.2415E+06 | -5.00E+02 | 1241.5 | -0.5 |
| 2484 | 8.05153E-07 | 0.324005223 | 1.2420E+06 | -5.00E+02 | 1242 | -0.5 |
| 2485 | 8.04829E-07 | 0.323744559 | 1.2425E+06 | -5.00E+02 | 1242.5 | -0.5 |
| 2486 | 8.04505E-07 | 0.32348421 | 1.2430E+06 | -5.00E+02 | 1243 | -0.5 |
| 2487 | 8.04182E-07 | 0.323224174 | 1.2435E+06 | -5.00E+02 | 1243.5 | -0.5 |
| 2488 | 8.03859E-07 | 0.322964452 | 1.2440E+06 | -5.00E+02 | 1244 | -0.5 |
| 2489 | 8.03536E-07 | 0.322705043 | 1.2445E+06 | -5.00E+02 | 1244.5 | -0.5 |
| 2490 | 8.03213E-07 | 0.322445946 | 1.2450E+06 | -5.00E+02 | 1245 | -0.5 |
| 2491 | 8.0289E-07 | 0.322187161 | 1.2455E+06 | -5.00E+02 | 1245.5 | -0.5 |
| 2492 | 8.02568E-07 | 0.321928688 | 1.2460E+06 | -5.00E+02 | 1246 | -0.5 |
| 2493 | 8.02246E-07 | 0.321670525 | 1.2465E+06 | -5.00E+02 | 1246.5 | -0.5 |
| 2494 | 8.01925E-07 | 0.321412673 | 1.2470E+06 | -5.00E+02 | 1247 | -0.5 |
| 2495 | 8.01603E-07 | 0.321155131 | 1.2475E+06 | -5.00E+02 | 1247.5 | -0.5 |
| 2496 | 8.01282E-07 | 0.320897898 | 1.2480E+06 | -5.00E+02 | 1248 | -0.5 |
| 2497 | 8.00961E-07 | 0.320640974 | 1.2485E+06 | -5.00E+02 | 1248.5 | -0.5 |
| 2498 | 8.00641E-07 | 0.320384359 | 1.2490E+06 | -6.00E+02 | 1249 | -0.5 |
| 2499 | 8.0032E-07 | 0.320128051 | 1.2495E+06 | -5.00E+02 | 1249.5 | -0.5 |
| 2500 | 0.0000008 | 0.319872051 | 1.2500E+06 | -5.00E+02 | 1250 | -0.5 |
| 2601 | 7.9968E-07 | 0.319616358 | 1.2505E+06 | -5.00E+02 | 1250.5 | -0.5 |
| 2502 | 7.99361E-07 | 0.319360971 | 1.2510E+06 | -5.00E+02 | 1251 | -0.5 |
| 2503 | 7.99041E-07 | 0.319105891 | 1.2515E+06 | -5.00E+02 | 1251.5 | -0.5 |
| 2504 | 7.98722E-07 | 0.318851116 | 1.2520E+06 | -5.00E+02 | 1252 | -0.5 |
| 2505 | 7.98403E-07 | 0.318596645 | 1.2525E+06 | -5.00E+02 | 1252.5 | -0.5 |
| 2506 | 7.98085E-07 | 0.31834248 | 1.2530E+06 | -5.00E+02 | 1253 | -0.5 |
| 2507 | 7.97766E-07 | 0.318088618 | 1.2535E+06 | -5.00E+02 | 1253.5 | -0.5 |
| 2508 | 7.97448E-07 | 0.31783506 | 1.2540E+06 | -5.00E+02 | 1254 | -0.5 |
| 2509 | 7.9713E-07 | 0.317581805 | 1.2545E+06 | -5.00E+02 | 1254.5 | -0.5 |
| 2510 | 7.96813E-07 | 0.317328853 | 1.2550E+06 | -5.00E+02 | 1255 | -0.5 |
| 2511 | 7.96495E-07 | 0.317076202 | 1.2555E+06 | -5.00E+02 | 1255.5 | -0.5 |
| 2512 | 7.96178E-07 | 0.316823854 | 1.2560E+06 | -5.00E+02 | 1256 | -0.5 |
| 2513 | 7.95862E-07 | 0.316571806 | 1.2565E+06 | -5.00E+02 | 1256.5 | -0.5 |
| 2514 | 7.95545E-07 | 0.316320059 | 1.2570E+06 | -5.00E+02 | 1257 | -0.5 |
| 2515 | 7.95229E-07 | 0.316068612 | 1.2575E+06 | -5.00E+02 | 1257.5 | -0.5 |
| 2516 | 7.94913E-07 | 0.315817465 | 1.2580E+06 | -5.00E+02 | 1258 | -0.5 |
| 2517 | 7.94597E-07 | 0.31566617 | 1.2585E+06 | -5.00E+02 | 1258.5 | -0.5 |
| 2518 | 7.94281E-07 | 0.315316068 | 1.2590E+06 | -5.00E+02 | 1259 | -0.5 |
| 2519 | 7.93966E-07 | 0.315065817 | 1.2595E+06 | -5.00E+02 | 1259.5 | -0.5 |
| 2520 | 7.93651E-07 | 793.6507937 | 1.2600E+06 | 1.26E+06 | 1260 | 1260 |

FIG. 11A

INTEGRATED SCANNING AND OCULAR TOMOGRAPHY SYSTEM AND METHOD

CROSS-REFERENCE TO RELATED APPLICATION

This is a regular patent application which claims priority under 37 C.F.R. 1.78(a) from U.S. Provisional Patent Application No. 60/392,330 filed Jun. 27, 2002, the full disclosure of which is incorporated herein by reference.

BACKGROUND OF THE INVENTION

The present invention relates generally to measurements of tissues, optical elements and other structures, and, more particularly, to methods and systems for integrated ocular tomography and scanning laser ablation.

Corneal shape corrective surgeries are commonly used to treat myopia, hyperopia, astigmatism, and the like. Procedures employing an excimer laser include LASIK (Laser Assisted In-Situ Keratomileusis), PRK (Photo Refractive Keratectomy) and LASEK (Laser Subepithelial Keratomileusis). During LASIK, a suction ring is typically placed over sclera tissue (the white part of the eye) to hold the eye firmly. A surgeon first uses a microkeratome with an oscillating steel blade to make a partial cut through a front surface of a cornea. A microkeratome automatically passing across a cornea creates a thin flap of clear tissue on a front central part of an eye. A suction ring is then removed, and a flap is lifted back to sufficiently expose tissue for ablation with a laser. A laser is programmed to correct a desired amount of visual effect, and directs a laser beam. A rapid, continuous emission of laser pulses removes very small precise amounts of corneal tissue. After irrigation with saline solution, a corneal flap is folded back to adhere to its original position.

Precise measurement of corneal thickness may benefit LASIK and other corneal shape corrective surgeries. An ability to monitor corneal thickness during surgery is desirable because it may facilitate improved control over ablation and may lead to more precise reshaping of a cornea. Further, in situ surgical tomographic measurement of a cornea may prevent over and under correction with ablation and excessive thinning of a cornea having associated problems such as kera ectasia.

Problems encountered with techniques for measuring a tomography of a cornea have often included a length of time required to measure corneal thickness and difficulty sampling corneal thickness over an area of tissue, as opposed to sampling thickness at a single point of tissue. Previous surgical systems have typically measured a central point or small central region of a cornea during surgery. Measuring a single point or small central region is less than ideal because such measurements typically represent only a small portion of a total treated area.

In light of the above it would be desirable to provide improved systems and methods for measuring a thickness of a cornea during surgery.

SUMMARY OF THE INVENTION

The present invention is generally directed to systems and methods measuring at least one reflecting surface of an object disposed along an optical path. A measured optical interference signal for each of at least three wavelengths of reflected light is used to determine a frequency component of a Fourier series. Frequency components of a Fourier series may be transformed to spatial components. Spatial components describe intensities and positions of light reflected along an optical path. Systems and methods of the present invention permit rapid measuring and monitoring of corneal thickness during surgery. Specific embodiments of the invention provide simple and efficient ways of measuring tomography of a cornea during ablation. The invention may do so by integrating an ablation device and a measurement apparatus into a single system.

In a first aspect the invention comprises a method of measuring a thickness of a tissue. The method includes reflecting at least three wavelengths of light from a tissue by directing a measurement light beam along an optical path toward a tissue. An interference signal for each of at least three wavelengths of reflected light is measured. A separation distance between positions of at least two reflecting tissue surfaces along an optical path is determined by combining measured interference signals.

In various embodiments, a measurement light beam may comprise at least three light wavelengths simultaneously directed along a path toward a tissue, and at least three interference signals may be measured simultaneously. Frequency components of a Fourier series may be determined from an interference signal for each of at least three wavelengths. Measured frequency components of a Fourier series may be transformed to spatial components. Spatial components describe positions and intensities of a light beam reflected from a tissue along an optical path. A tomography of a tissue may be determined by directing a measurement beam to several locations of a tissue. Locations may have at least two reflecting tissue surfaces along an optical path. A light beam may be scanned from a first location to a second location. A first location and a second location may be among locations used to determine a tomography of a tissue.

In some embodiments the invention comprises a method of treating a tissue. A desired shape is formed in a tissue by directing an ablative light beam toward a tissue. A tissue reflects at least three wavelengths of light from a measurement light beam directed along an optical path. An interference signal for each of at least three wavelengths of reflected light is measured. Positions of at least two reflecting tissue surfaces along a optical path are determined by combining measured interference signals while an ablative light beam is directed toward a tissue.

In additional embodiments a measurement light beam may comprise at least three wavelengths simultaneously directed along a path toward a tissue and at least three interference signals may be measured simultaneously. Frequency components of a Fourier series may be determined from an interference signal for each of at least three wavelengths. Measured frequency components of a Fourier series may be transformed to spatial components. Spatial components may describe positions and intensities of a light beam reflected from a tissue along an optical path.

In some embodiments, the invention comprises a method of treating a tissue. An ablative beam for ablating a tissue is directed via a scanning device to a tissue. A measurement beam for measuring a profile of a tissue is directed via a scanning device to a tissue. A path of an ablative beam and a path of a measurement beam are substantially concentric as directed onto a tissue.

In specific embodiments a path of an ablative beam and a path of a measurement beam may be substantially coaxial as directed onto a tissue. A tissue may be measured intermittently at time intervals between instances of ablation. A measurement beam for measuring a thickness of a tissue may be directed to a tissue via a scanning device.

In another aspect, the invention comprises a system for measuring a thickness of a tissue. A system comprises a light source emitting a measurement light beam directed along an optical path toward a tissue. At least three wavelengths of a measurement light beam reflect from a tissue. An interferometer generates an interference signal for each of at least three wavelengths of a measurement light beam reflected from a tissue. A processor determines a separation distance between positions of at least two reflecting tissue surfaces along an optical path by combining interference signals.

In some embodiments a measurement light beam may comprise at least three light wavelengths simultaneously directed along a path toward a tissue, and at least three interference signals may be measured simultaneously. An interference signal of each of at least three light wavelengths may be used to determine frequency components of a Fourier series. A processor may transform frequency components of a Fourier series to spatial components. Spatial components may describe positions and intensities of a light beam reflected from a tissue along an optical path. An optical system may direct a measurement beam to several locations of a tissue so as to determine a tomography of a tissue at locations having at least two reflecting tissue surfaces along an optical path. An optical system may scan a light beam from a first location to a second location. A first location and a second location may be among locations used to determine a tomography of a tissue.

In many embodiments the invention comprises a system for treating a tissue. A system comprises an ablative light source emitting an ablative light beam. A light source emits a measurement light beam directed along an optical path toward a tissue. At least three wavelengths of a measurement light beam reflect from a tissue. An interferometer generates an interference signal for each of at least three wavelengths of a measurement light beam reflected from a tissue. A processor controls an ablative light beam and determines positions of at least two reflecting tissue surfaces along an optical path by combining interference signals.

In specific embodiments a measurement light beam may comprise at least three wavelengths simultaneously directed along an optical path toward a tissue, and at least three interference signals may be measured simultaneously. An interference signal of each of at least three wavelengths may be used to determine a frequency component of a Fourier series. A processor may transform frequency components of a Fourier series to spatial components describing positions and intensities of a light beam reflected from a tissue along an optical path.

In some embodiments the invention comprises an apparatus for treating tissue. An ablative light source produces an ablative light beam. A measurement light source produces a measurement light beam. A scanner receives an ablative light beam from an ablative light source and a measurement light beam from a measurement light source. A scanner includes optical elements directing an ablative beam and a measurement beam to locations across a tissue so as to ablate a tissue with an ablative beam and measure a profile of a tissue with a measurement beam. A path of an ablative beam and a path of a measurement beam are substantially concentric at a tissue. A path of an ablative beam and a path of a measurement beam may be substantially coaxial as directed onto a tissue. A processor may be electrically connected with an ablative light source and a measurement light source. A processor may control an ablative light beam and a measurement light beam.

In specific embodiments the invention comprises an apparatus for treating tissue. An ablative light source produces an ablative beam. A beam delivery device directs an ablative beam onto a tissue. A microscope has a viewing port. An optical pachymeter emits a measurement light beam directed along an optical path toward a tissue. At least three wavelengths of a light beam reflect from a tissue. An optical pachymeter comprises an interferometer generating an interference signal for each of at least three wavelengths of a measurement light beam reflected from a tissue. A pachymeter includes a processor determining a separation distance between positions of at least two reflecting tissue surfaces along an optical path by combining interference signals. A measurement light beam may comprise at least three wavelengths simultaneously directed along a path toward a tissue, and at least three interference signals may be measured simultaneously. An interference signal of each of at least three wavelengths may be used to determine frequency components of a Fourier series. A processor may transform frequency components of a Fourier series to spatial components. Spatial components may describe positions and intensities of a light beam reflected from a tissue along an optical path.

In another aspect the present invention comprises a method of measuring a separation distance between positions of at least two reflections along an optical path. At least three wavelengths of light are reflected at the positions by directing a measurement light beam along an optical path. An interference signal for each of the at least three wavelengths of reflected light is measured. A separation distance between positions of at least two reflections along an optical path is determined by combining interference signals.

BRIEF DESCRIPTION OF THE DRAWINGS

FIGS. 11A–11D illustrate dimensions, wavelengths and signals in accordance with an embodiment of the present invention.

DESCRIPTION OF THE SPECIFIC EMBODIMENTS

The present invention is particularly useful for enhancing accuracy and efficacy of laser eye surgical procedures, such as photorefractive keratectomy (PRK), phototherapeutic keratectomy (PTK), laser assisted in situ keratomileusis (LASIK), laser subepithelial keratomileusis (LASEK) and the like. Preferably, the present invention can provide enhanced optical accuracy of refractive procedures by improving a corneal ablation of a refractive treatment program. Hence, while the system and methods of the present invention are described primarily in a context of a laser eye surgery system, it should be understood techniques of the present invention may be adapted for use in alternative eye treatment procedures and systems such as spectacle lenses, intraocular lenses, contact lenses, corneal ring implants, collagenous corneal tissue thermal remodeling, and the like.

Systems and methods of the present invention permit rapid measurements of an object having reflecting and scattering surfaces, and are able to rapidly measure a thickness and a tomography of a cornea. Systems and methods of the present invention may be integrated into a surgical laser for sculpting a corneal surface. In embodiments using several wavelengths of light and spectral decomposition techniques corneal thickness may be obtained very rapidly.

As used herein an "optical tissue surface" may encompass a theoretical tissue surface derived from an optical measurement of light refraction of an eye (exemplified by wavefront sensor data and manifest refraction data), an actual tissue surface, and/or a tissue surface formed for purposes of treatment (for example, by incising corneal tissues so as to allow a flap of the corneal epithelium to be displaced and expose the underlying stroma during a LASIK procedure).

Figure 1:
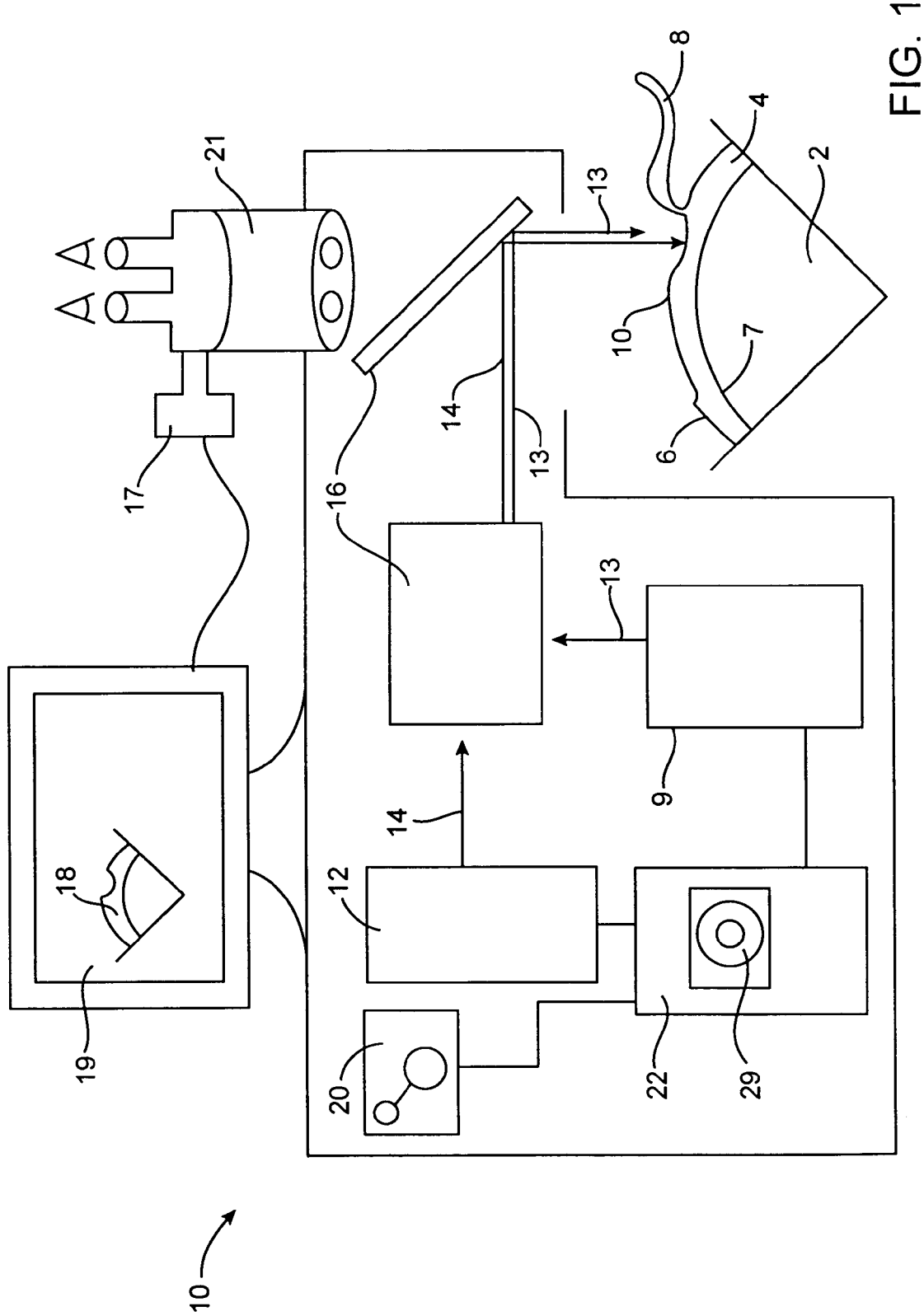
FIG. 1 illustrates a laser eye surgery system incorporating the present invention.

A laser ablating a surface of an eye is illustrated in FIG. 1. A laser eye surgery system 10 includes a laser module 12 that produces a laser beam 14. An eye 2 is illustrated in cross section as being ablated by a laser system 10 having a laser module 12 emitting a beam 14 of an ablative light energy. An eye 2 has a cornea 4. A cornea 4 has a front surface 6 and a back surface 7. During surgery a flap 8 of tissue is often excised from a cornea 4. A bed 10 of remaining tissue is exposed when a flap 8 is resected. In some instances, a thickness between a front surface 6 and a back surface 7 may vary across a corneal tissue. Laser delivery optical system 16 is in a path of laser beam 14. Delivery optical system 16 direct laser beam 14 to an eye 2. An input device 20 is used to align laser system 10 in relation to an eye 2. A microscope 21 is often used to image a cornea 4 of an eye 2. A display 19 is viewable by a user of system 10. A processor 22 of system 10 includes a tangible media 29. A tomography system 9 has a measurement beam 13. Elements of delivery optical system 16 are common to both measurement beam 13 and laser beam 14. In various embodiments, a laser eye surgery system 10 includes at least some portions of a Star S3 Active Trak® Excimer Laser System available from VISX, Incorporated of Santa Clara, Calif.

While an input device 20 is here schematically illustrated as a joystick, a variety of input components may be used. Suitable input components may include trackballs, touch screens, or a wide variety of alternative pointing devices. Still further alternative input components include keypads, data transmission mechanisms such as an Ethernet, intranet, internet, a modem, or the like.

A laser module 12 generally comprises an excimer laser and ideally comprises an argon-fluoride laser producing pulses of laser light having a wavelength of approximately 193 nm. A pulse of laser light typically has a fixed pulse duration having a full width half maximum (FWHM) of about 15 nano seconds during a treatment. Laser module 12 is preferably designed to provide a feedback-stabilized fluence at the patient's eye, delivered via delivery optical system 16. The present invention may also be useful with alternative sources of ultraviolet or infrared radiation, particularly those adapted to controllably ablate a corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193–215 nm) such as those described in U.S. Pat. Nos. 5,144,630 and 5,742,626, Borsuztky et al., "Tunable UV Radiation at Short Wavelengths (188–240 nm) Generated by Sum Frequency Mixing in Lithium Borate", *Appl. Phys.* 61:529–532 (1995), and the like. Laser energy may comprise a beam formed as a series of discreet laser pulses. A variety of alternative lasers might also be used. Hence, although an excimer laser is the illustrative source of an ablative beam, other lasers may be used in the present invention.

Laser module 12 and delivery optical system 16 will generally direct laser beam 14 to an eye 2 of patient under direction of a processor 22. Processor 22 will often selectively adjust laser beam 14 to expose portions of a cornea to pulses of laser energy so as to effect a predetermined sculpting of a cornea and alter refractive characteristics of an eye. In many embodiments, both laser 14 and a delivery optical system 16 will be under computer control of processor 22 to effect a desired laser sculpting process, with processor 22 effecting (and optionally modifying) a pattern of laser pulses. A pattern of pulses may be summarized in a treatment table listing of machine readable data of a tangible media 29. A treatment table may be adjusted according to feedback input into processor 22 from an automated cornea shape analysis system (manually input into processor 22 by a system operator) in response to feedback data provided from an ablation monitoring system feedback system.

Feedback is provided by a rapid tomographic measurement system 9 integrated with a laser treatment system 10, and processor 22 may continue and/or terminate a sculpting treatment in response to feedback, and may optionally also modify a planned sculpting based at least in part on feedback. Information related to a surgical procedure is shown on a display 19. Information on display 19 may include a profile in cross section 18 of a corneal tissue as feedback measured by a rapid tomographic measurement system 9. Display 19 may also show a video image of a cornea 4 as seen through a microscope 21. A CCD camera 17 mounted to a microscope 21 is in electrical communication with a display 19.

Laser beam 14 may be adjusted to produce a desired sculpting using a variety of alternative mechanisms. A laser beam 14 may be selectively limited using one or more variable apertures. An exemplary variable aperture system having a variable iris and a variable width slit is described in U.S. Pat. No. 5,713,892, the full disclosure of which is incorporated herein by reference. A laser beam may also be tailored by varying a size and offset of a laser spot from an axis of an eye, as described in U.S. Pat. No. 5,683,379, and as also described in co-pending U.S. patent application Nos. 08/968,380, filed Nov. 12, 1997; and 09/274,999 filed Mar. 22, 1999, the full disclosures of which are incorporated herein by reference.

Still further alternatives are possible, including scanning a laser beam over a surface of an eye and controlling a number of pulses and/or dwell time at each location, as described, for example, by U.S. Pat. No. 4,665,913 (the full disclosure of which is incorporated herein by reference); using masks in an optical path of laser beam 14 which ablate to vary a profile of a beam incident on a cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea as described in U.S. Pat. Nos. 6,319,247; 6,280,435; and 6,203,539, the full disclosures of which are incorporated herein by reference; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control a distribution of energy within a laser beam, as described in U.S. Pat. Nos. 5,646,791 and 5,912,779 the full disclosures of which are incorporated herein by reference. An ablation effluent evacuator/filter, and other ancillary components of a laser surgery system that are not necessary to an understanding of the invention, which may be optionally employed, need not be described in detail for an understanding of the present invention.

Processor 22 may comprise (or interface with) a conventional PC system including standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any methods of the present invention. Tangible storage media 29 may comprise a floppy disk, an optical disk, a data tape, a volatile or non-volatile memory, or the like, and a processor 22 will include memory boards and other standard components of modern computer systems for storing and executing a computer program code. Tangible storage media 29 may optionally embody wavefront sensor data, wavefront gradients, a wavefront elevation map, a treatment map, a corneal topography map, a measurement of a refraction of an eye, and an ablation table.

Figure 2:
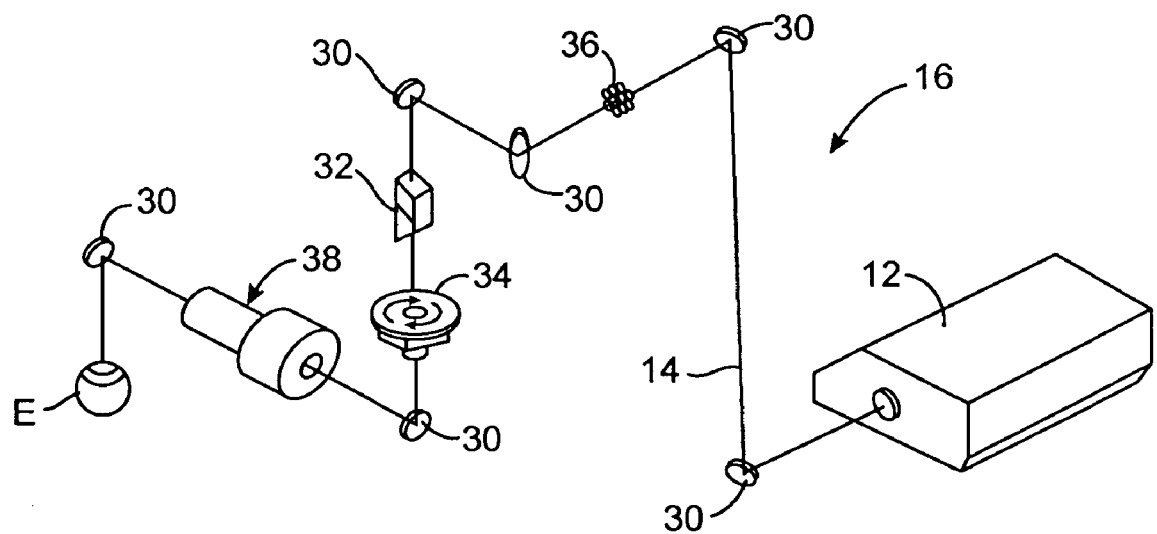
FIGS. 2 and 3 schematically illustrate a laser beam delivery system for selectively directing a laser beam onto a corneal tissue for incorporation with the present invention.

Referring now to FIG. 2, a laser beam delivery system 16 for directing a laser beam 14 at an eye 2 will often include a number of mirrors 30, as well as one or more temporal integrators 32 which may adjust (or otherwise tailor) an energy distribution across a laser beam. Laser module 12 will often comprise an excimer laser as described above.

In an exemplary embodiment, a variable aperture 34 changes a diameter and/or slot width to profile laser beam 14, ideally including both a variable diameter iris and a variable width slot. A prism 36 separates laser beam 14 into a plurality of beamlets, which may partially overlap on eye 2 to smooth edges of an ablation or "crater" formed from each pulse of a laser beam.

Figure 3:
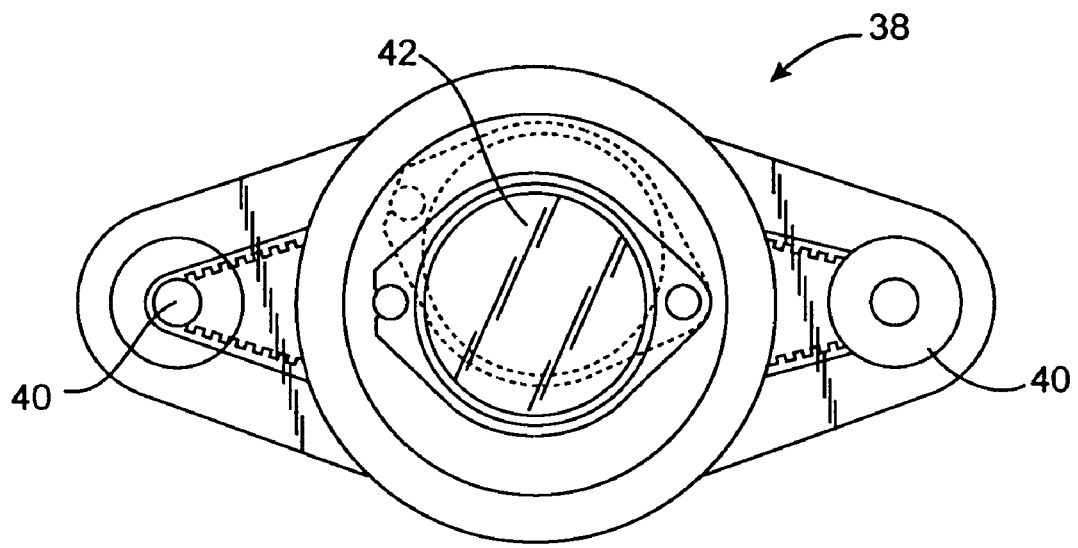

Referring now to FIGS. 2 and 3, an offset module 38 includes motors 40 which vary an angular offset of an offset lens 42, and which also change a radial orientation of an offset. Hence, offset module 38 can selectively direct laser beam 14 at a desired lateral region of a cornea. A system and method for using a laser beam delivery system 16 and an offset module 38 are more fully described in U.S. Pat. Nos. 6,331,177; 6,203,539; 5,912,775; and 5,646,791 the full disclosures of which are incorporated herein by reference.

Figure 4:
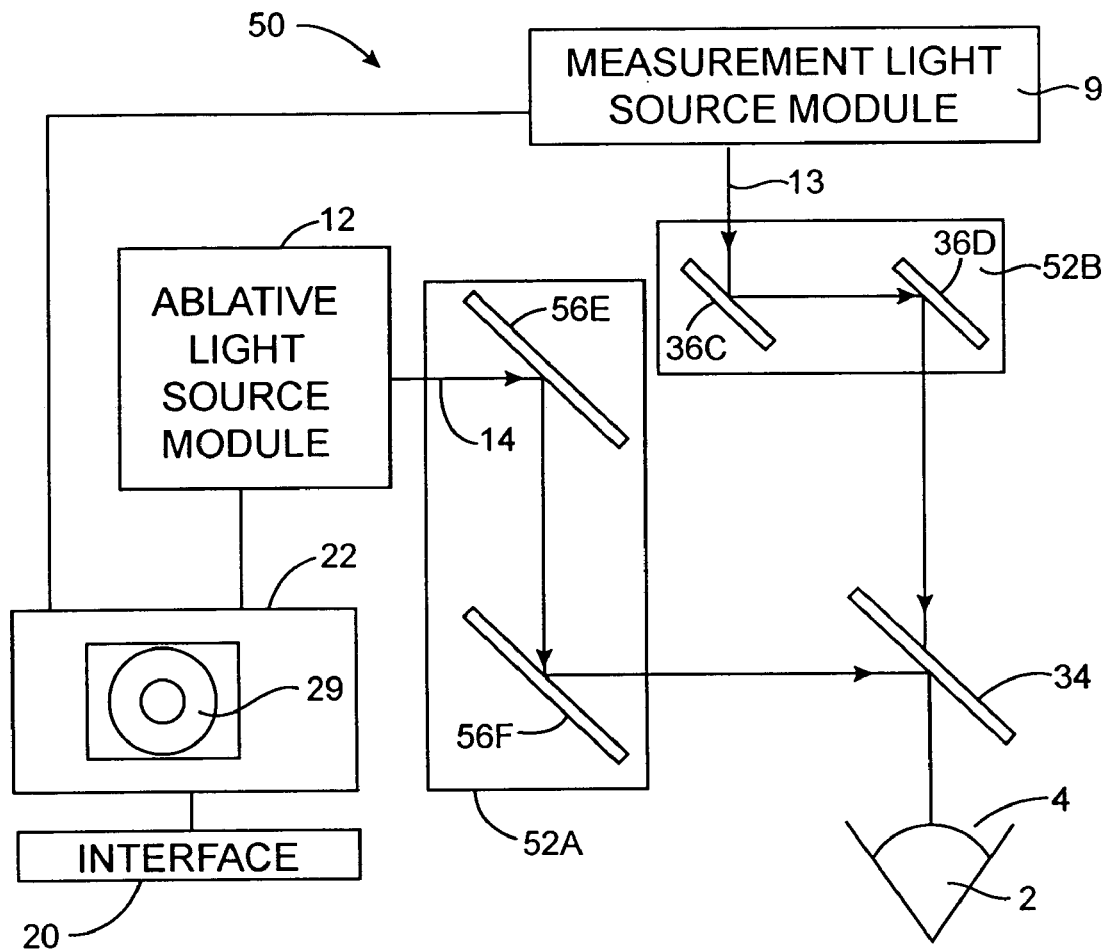
FIG. 4 is a schematic view of a laser delivery system incorporating a tomography system in accordance with an embodiment of the invention.

FIG. 4 illustrates an embodiment of an integrated scanning laser and ocular tomography system 50 having separate scanning modules 52A and 52B. Scanning device 52A having mirrors 56E and 56F scans ablative light beam 14 over a cornea 4 of an eye 2. Scanning device 52B scans a measurement light beam 13 over a cornea 4 of an eye 2. With an embodiment as in FIG. 4, paths of an ablative light beam 14 and a measurement light beam 13 may be combined after passing through scanning modules 52A and 52B. It is understood that the scanning modules 52A and 52B may include any suitable arrangement of optical elements for delivering beams to the cornea 4. Several known methods and systems for ablating tissue surfaces with laser beams can be combined with a measurement light source module and a scanning module as illustrated in FIG. 4.

Figure 5:
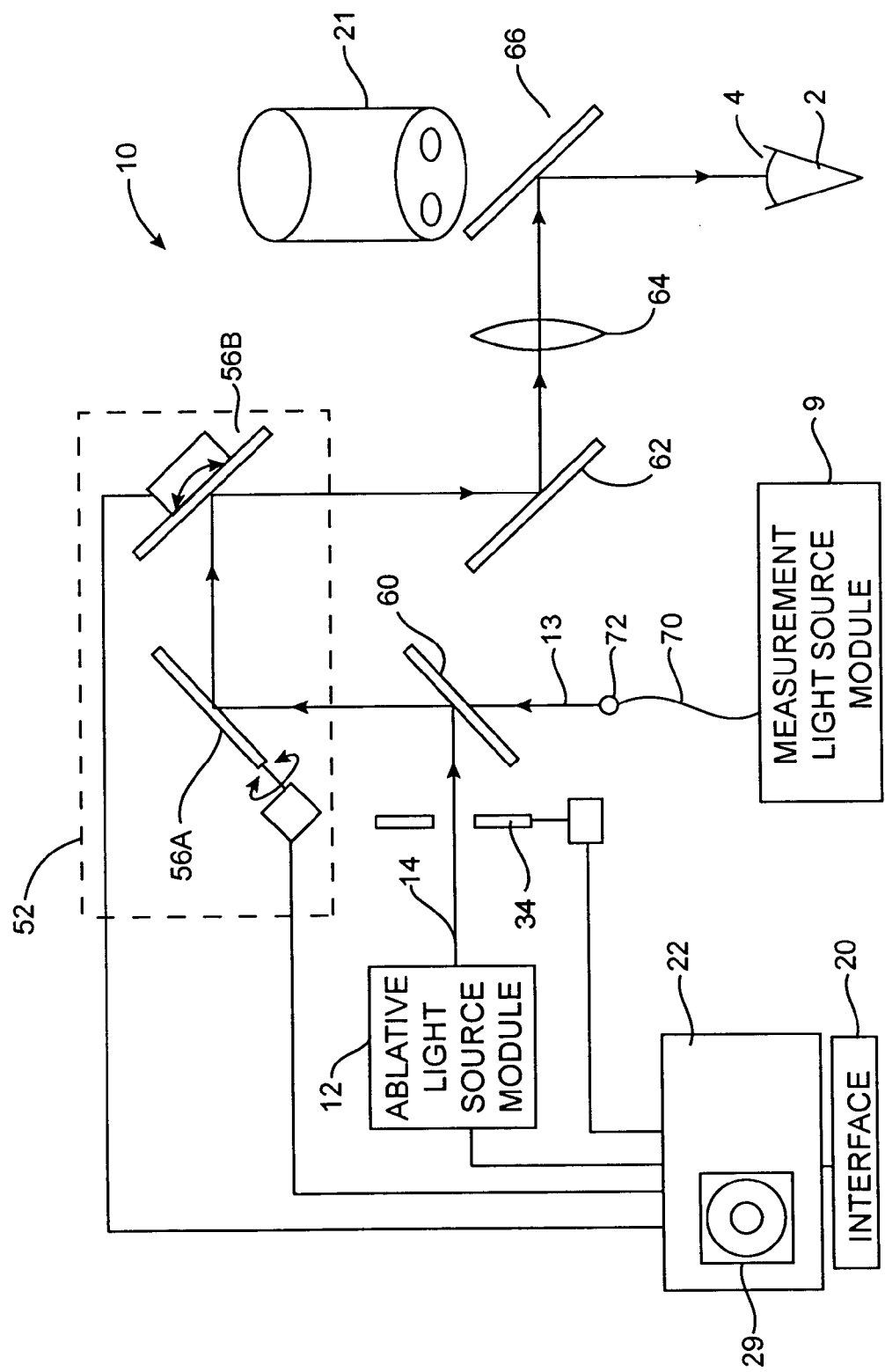
FIG. 5 is a schematic view of an alternate laser delivery system for incorporating a tomography system in accordance with another embodiment of the present invention.

FIG. 5 illustrates an integrated scanning and ocular tomography system 20 including a scanning device 52 for delivering an ablative beam 14 of light energy from an ablative light energy source module 12 to a cornea 4 of an eye 2. An ablative light energy source module 12 typically includes a laser as the light energy source as described above. A measurement beam 13 of light energy from a measurement light energy source module 9 also passes through the scanning device 52 which delivers a measurement beam 13 to a cornea 4. A measurement light energy source module 9 will typically include a source of light energy and optical elements for generating measurement data. An ablative beam 14 and measurement beam 13 typically have different wavelengths. For example, an ablative light energy beam 14 will typically have a wavelength of about 200 nm, preferably 193 nm as described above, and measurement beam 13 will typically have a wavelength between about 700 nm and 1700 nm. Paths of laser beam 14 and measurement beam 13 are combined with a mirror 60 before scanning device 52. Mirror 60 preferably has a dielectric coating selectively reflecting ultraviolet light and passing visible light. Such mirrors are well known in the art. For simplicity, a scanning device 52 is shown to include a pair of mirrors 56A, 56B. A processor 22 is provided to control operation of the system 10 as described above, and is in electrical communication with scanning mirror pair 56A, 56B.

In an embodiment of a laser delivery system integrated with a tomography system, an ablative beam 14 and measurement beam 13 are concentric so that ablation and measurement may take place at the same location. To further improve accuracy, an ablative beam 14 and measurement beam 13 are desirably coaxial and concentric as directed toward a cornea 4. A coaxial and concentric arrangement of measurement beam 13 and ablative beam 14 eliminates axial displacement errors that may be caused by angular variations between the beams. A terminus 72 of optical fiber 70 emits measurement light beam 13. A scanning device 52 includes optical elements configured to focus ablative and measurement beams confocally and coaxially. For example, lens 64 forms an image of an aperture in module 34 near a surface of cornea 4, and lens 64 also forms an image of a terminus 72 of optical fiber 70 near a surface of cornea 4. Mirrors 62 and 66 reflect light from measurement beam 13 and ablative light beam 14 to direct both measurement light beam 13 and ablative light beam 14 to a cornea 4. Use of the scanning device 52 to deliver both an ablative beam 14 and a measurement beam 13 may provide effective delivery of both beams confocally and coaxially, and avoids a need to introduce two separate sets of beam delivery apparatus.

Processor 22 is in electrical communication with a measurement light source module 9 to control generation of a measurement beam 13 and to process measurement data. For example, a measurement beam 13 may generate an interference pattern with reflection from a cornea 4 and reflection from a reference surface. Processor 22 processes measured interference patterns to extract tomography data of a cornea 4, preferably at a sufficient processing rate to allow real time monitoring of ocular tomography during ablation by ablative beam 14. For instance, a processing rate may be higher than a pulse repetition rate of a laser in an ablative light source module generating ablative beam 14. In this way, the ocular tomography can be monitored by processor 22 via measurement light source module 9 on a pulse-by-pulse basis. As a result, substantially simultaneous ablation and measurement may be accomplished.

A target tomographic shape of a cornea 4 may be preset based on a diagnosis of the patient, and be stored in a memory of processor 22. A processor 22 may compare measured tomography with a target tomography for a tissue shape in real time to determine an ablative depth needed to achieve a targeted tomography. A processor 22 may dynamically direct operation of an ablative light source module 12 and a scanning device 52 to adjust energy and/or positioning of ablative beam 14 and scan ablative beam 14 across a cornea 4 at desired locations with appropriate intensity levels to achieve a desired beam exposure and targeted correction in real time.

A processor 22 can also provide temporal control of the delivery of the ablative beam 14 and measurement beam 13. Although ablation and measurement can take place simultaneously, the ablative process may perturb the measurement beam 13 and lead to inaccurate measurements. Some embodiments provide temporal interleaving of ablation and measurement to ensure accuracy. A processor 22 may direct operation of an ablative light source module 12 and measurement light source module 9 to produce an intermittent ablative beam 14 and intermittent measurements of beam 13 that alternate in time. Alternately, a measurement beam 13 may be measured continuously, while an ablative beam 14 is intermittent. A processor 22 may direct operation of a measurement light source module to take measurements in time intervals between pulses of an intermittent ablative beam 14.

A variety of methods of generating and using a measurement beam 13 for tomography measurement may be adapted to a laser system 10. A measurement beam 13 may be generated by a variety of sources including, for instance, a white light source, a super-luminescent diode, and a tunable laser source providing laser light tuned to a specific wavelength. By way of example, the following describes a Fourier reconstruction interferometer apparatus and an optical coherence tomography apparatus. Each apparatus includes a light source and optical elements that comprise a measurement light source module 9 emitting a measurement beam 13 as described above.

Fourier Reconstruction Interferometer

Figure 6:
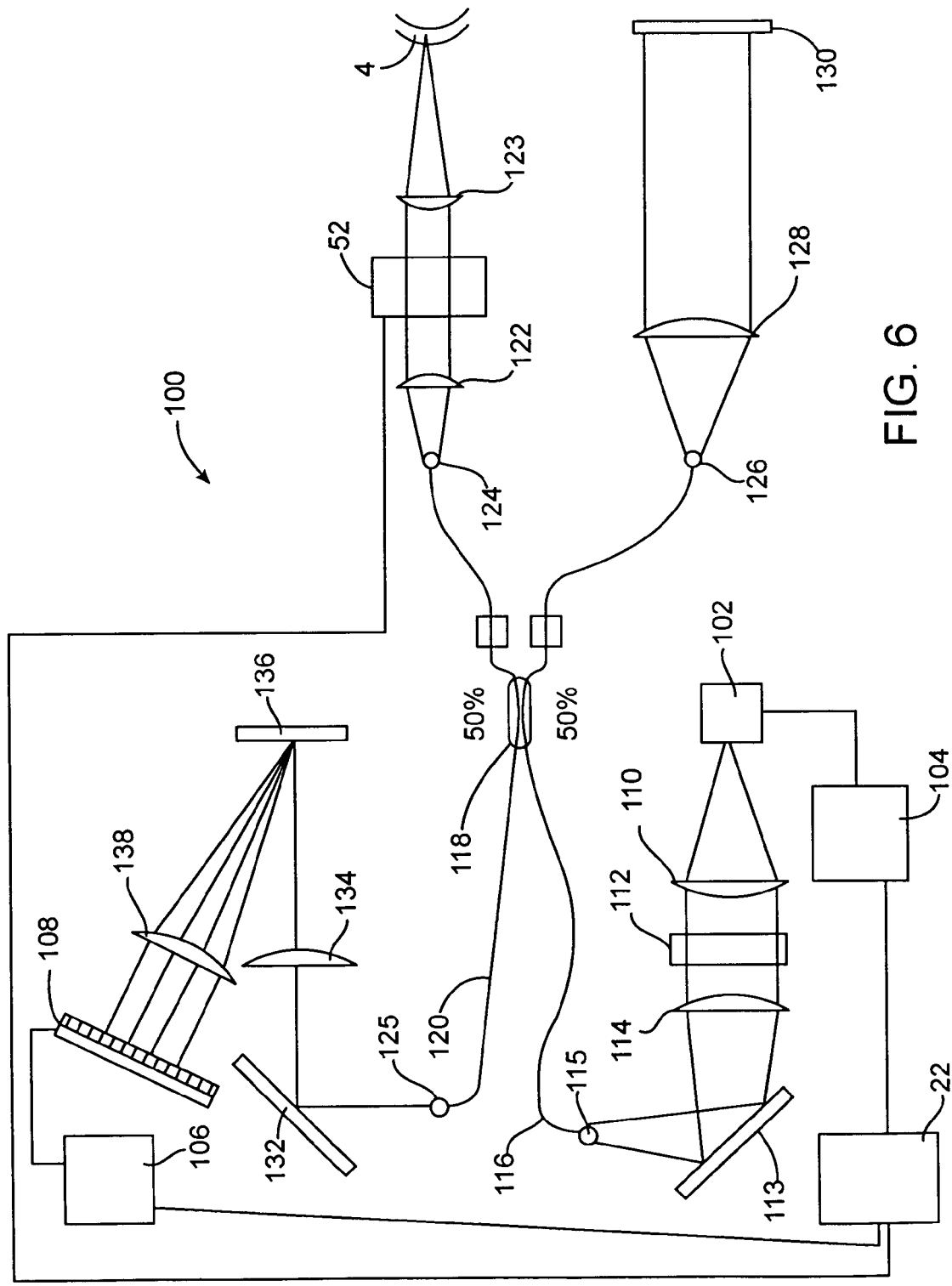
FIG. 6 is a schematic illustration of a Fourier reconstruction tomography system for rapidly measuring a shape and thickness of a cornea in accordance with an embodiment of the present invention.

FIG. 6 illustrates an embodiment of a tomographic measurement system that may be integrated with a laser system 10 as described above. A Fourier reconstruction interferometer apparatus 100 measures a tomography of corneal tissue. Many elements of interferometer apparatus 100 are preferably comprised within light source module 9 as described above. A processor 22 is electrically connected with a scanning module 52 as described above. In an alternate embodiment surface topography may be measured. A super luminescent diode 102 emits a beam of light energy and is electrically connected with a super luminescent diode driver 104. A super luminescent diode driver 104 is electrically connected with processor 22. While any super luminescent diode emitting any wavelength of light can be used, a preferred diode emits infrared light at about 1500 nm. A commercially available super luminescent diode 102 and diode driver may be comprised within a single subsystem. For example, a LightPAK™ LP-2000 intelligent optical source available from Fiberbyte of Adelaide, SA, Australia includes many super luminescent diodes and a diode driver. A super luminescent diode emits light at about 1500 nm and has a full width half maximum (FWHM) of about 40 nm. An InGaAs linear image sensor 108 is in electrical communication with a sensor module 106 having a driver amplifier circuit and control subsystem. Examples of a suitable linear image sensor and sensor module are a G8161-512 S Linear Imaging Sensor and a C7557 Sensor Module, both available from Hamamatsu of Hamamatsu City, Japan.

A lens 110 collimates light emitted by super luminescent diode 102. An etalon 112 selectively passes frequencies of light emitted by super luminescent diode 102. The frequencies of light passed by an etalon 112 are frequency components of a Fourier series. A lens 114 focuses light into a first end 115 of first optical fiber 116. An optional mirror 113 between lens 114 and first end 115 reflects focused light. A 50/50 coupler 118 combines light from a first optical fiber 116 with light from a second optical fiber 120. Light entering a first optical fiber 116 is enters a second optical fiber 120 at 50/50 coupler 118 and is emitted from a first end 124 of second optical fiber 120. Lens 122 collimates light emitted by a first end 124. Collimated light passes through scanning module 52 as described above. A lens 123 images and focuses emitted light from scanning module 52. Imaged and focused light is incident on cornea 4. Light reflected from cornea 4 travels through lenses 122 and 123, enters a first end of a second optical fiber 120, and is emitted by a second end 125 of second optical fiber 120.

A lens 128 collimates light emitted by a second end 126 of a first optical fiber 116. A mirror 130 reflects light back toward lens 128 and a second end 126. Light reflected from mirror 130 is combined with light reflected from cornea 4 at 50/50 coupler 118. Combined light is emitted from a second end 125 of a second fiber 120. An optional mirror 132 reflects light toward a lens 134. A lens 134 collimates light emitted by a second end 125. A grating 136 diffracts light. A lens 138 focuses light onto a linear image detector 108 as described above. A separation distance between lens 138 and grating 136 may typically be about a focal length of lens 138, and a separation distance between a lens 138 and a linear image sensor 108 may typically be about a focal length of a lens 138. Alternate embodiments may use different optical components and separation distances to separate wavelengths of light at a detector.

Cornea 4 is positioned so that an optical path length of light traveling to a reference mirror 130 from source 102 will be near an optical path length of light traveling to a cornea 4 from a source 102. A boundary of a measured tissue, for example an apex of a front surface of a cornea, is positioned with control and at a location having an optical path length near that of a reference mirror 130.

An etalon can be used to provide several light frequency components and wavelengths of a Fourier series. For an illustrative optical path length of an etalon of 2 mm and an illustrative wavelength of light of 800 nm, an integer number of 2500 oscillations of light will occur. Additional light wavelengths are spaced at spectral line widths of about 0.32 nm. For a light source having a full width half maximum of 32 nm and a central wavelength of about 800 nm, about 100 frequencies of light are available as frequency components of a Fourier series. An inverse Fourier transform is made with frequencies of light that are measured. While over 2500 wavelengths are theoretically possible, an inverse Fourier transform will provide valuable information even with a band of wavelengths having a limited number of measured frequencies. An inverse Fourier transform of measured interference signals for wavelengths having spectral line widths of 0.32 nm will determine intensities of reflected light at 0.32 nm increments along an optical path.

Frequencies and wavelengths of light can be generated at any wavelength. For example, white light having a wavelength between about 400 and 800 nm may be used. Wavelengths at about 1500 nm are desirable as longer wavelengths scatter light less than shorter wavelengths and will penetrate into a tissue structure. Wavelengths at about 10 um may be used to a measure topography of a surface appearing rough and diffuse when illuminated with shorter wavelengths of light, for example visible wavelengths.

An etalon of any length and finesse can be used to generate frequency components at any desired spectral line width. While at least 3 wavelengths of reflected light are used to generate frequency components, in general more frequency components produce more accurate measurements. In some embodiments 10 or more, wavelengths of light are reflected from a cornea to generate frequency components. As described above 100 or more wavelengths of light may be generated and reflected from a cornea. A linear image sensor may have at least 500 pixel elements, and 200 or more wavelengths may be generated and reflected from a tissue. Light from a broad spectral source, for example a white light source, may be passed though an etalon to generate light having thousands of frequency components of a Fourier series for reflecting from a cornea.

Figure 7:
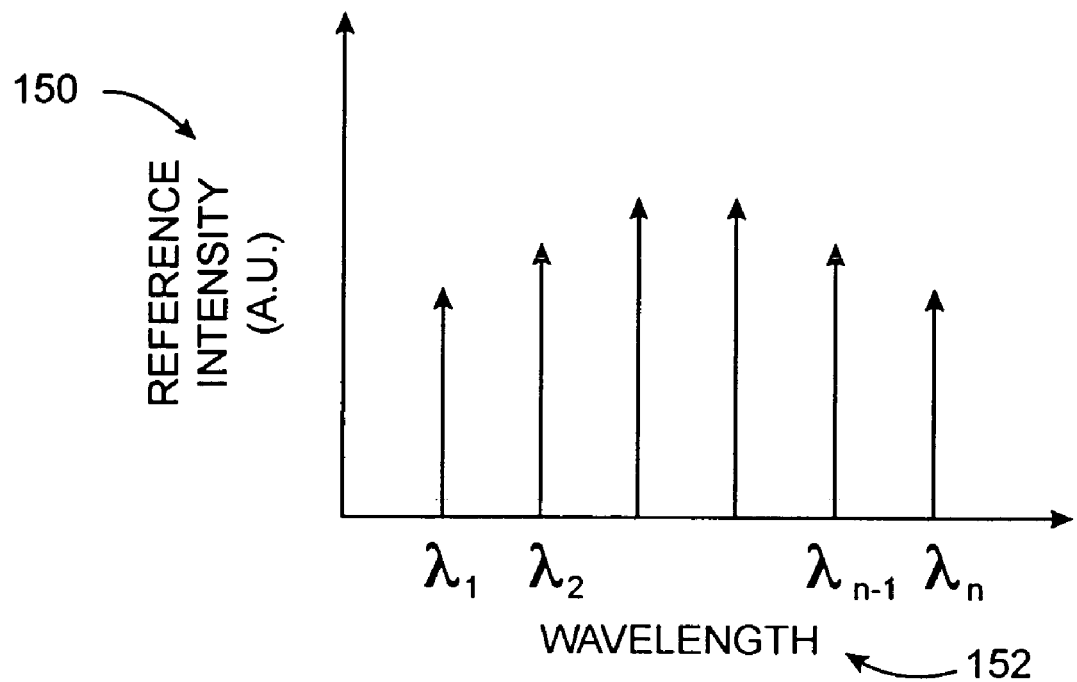
FIG. 7 illustrates an reference spectrum obtained from a calibration measurement of a system as in FIG. 6, in accordance with an embodiment of the present invention.

As illustrated in FIG. 7, reference intensity 150 in arbitrary units (A.U.) is measured for a wavelength 152 of several wavelengths of light energy emitted by a super luminescent diode. Such a measurement may be taken with light reflected from a reference mirror 130 while a reflecting surface such as a cornea 4 is removed from an optical path of light emitted from a first end 124 of a second optical fiber 120 as described above. Reference intensity 150 generally matches a spectral distribution of light energy emitted by a super luminescent diode 102 as described above. While a value for any wavelength can be measured, wavelengths within a full width half maximum band of wavelengths emitted by a superluminescent diode are often measured.

Figure 8:
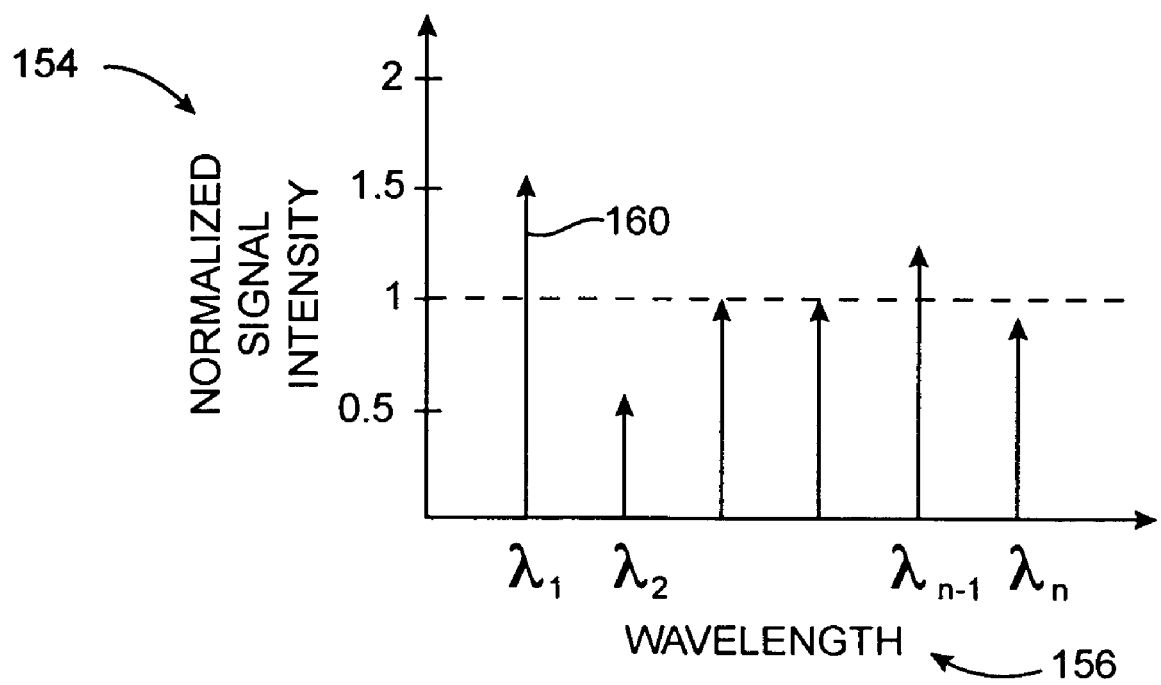
FIG. 8 illustrates an interference spectrum obtained from a cornea measurement with a system as in FIGS. 6 and 7.

To determine a tomography of an object, a cornea is positioned along an optical path of emitted light as described above. Light emitted from a super luminescent diode is reflected and combined as described above. As shown in FIG. 8, an interference signal 160 for each of several wavelengths of light 156 is measured at linear image detector 108 with linear image sensor 108 and sensor module 106, as described above. Values above a reference intensity value for a given wavelength result from constructive interference and values below a reference intensity value for a given wavelength result from destructive interference. Measured signals are normalized with respect to reference values as described above to provide a normalized signal intensity 154 for each of several wavelengths 156.

Figure 9:
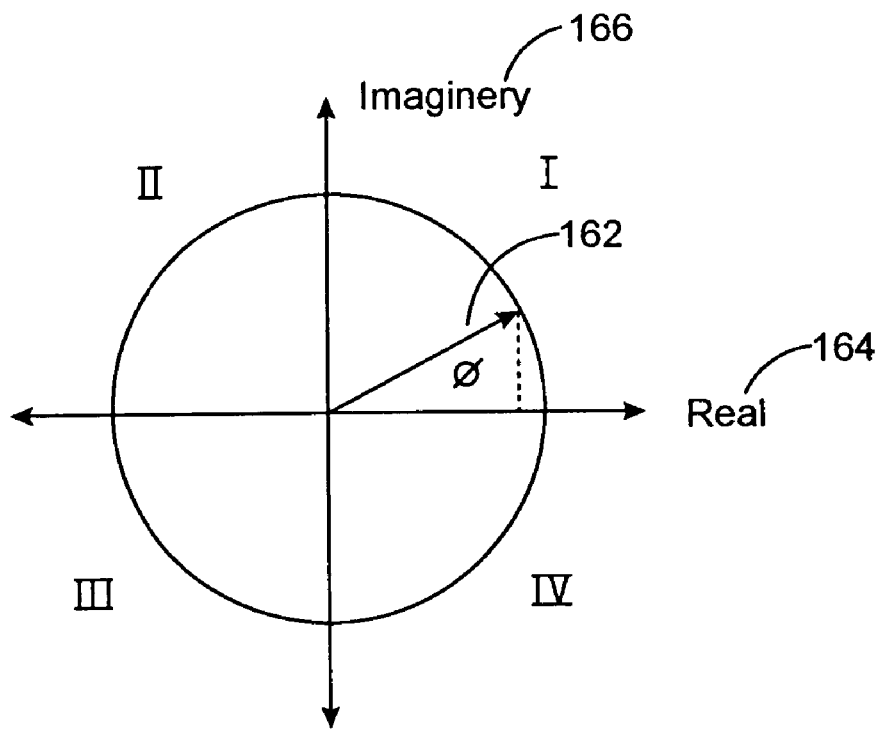
FIG. 9 illustrates components of an interference signal in accordance with an embodiment of the present invention.

A phase plot of a reflected tissue component 162 of interference signal 160 at a wavelength of light is illustrated in FIG. 9. An intensity of a reference signal as described above is modulated by light reflected from a tissue. A phase plot of a reflected tissue component 162 of an interference signal 160 has a real component 164 and an imaginary component 166. A real component 164 is measurable by linear image sensor 108 as a modulation of a reference signal as described above. An imaginary component 166 of a reflected tissue component 162 may be determined from a real component 164. In an embodiment, an angle of an imaginary component 166 is determined with an arccosine of a real component 164. In some embodiments a magnitude of a reflected tissue component 162 may be determined by selecting a maximum amplitude modulation from among several normalized signal intensities having similar reflective properties in tissue.

Each interference signal has an associated wavelength of light. A spatial frequency of light is determined by a speed of light in tissue and its oscillation frequency. An index of refraction, n, determines a speed of light in a tissue. A cornea has an index of refraction of about 1.377 and an aqueous humor of an eye has an index of refraction of about 1.33. A spatial frequency for a wavelength of light is calculated for an appropriate index of refraction.

Figure 10:
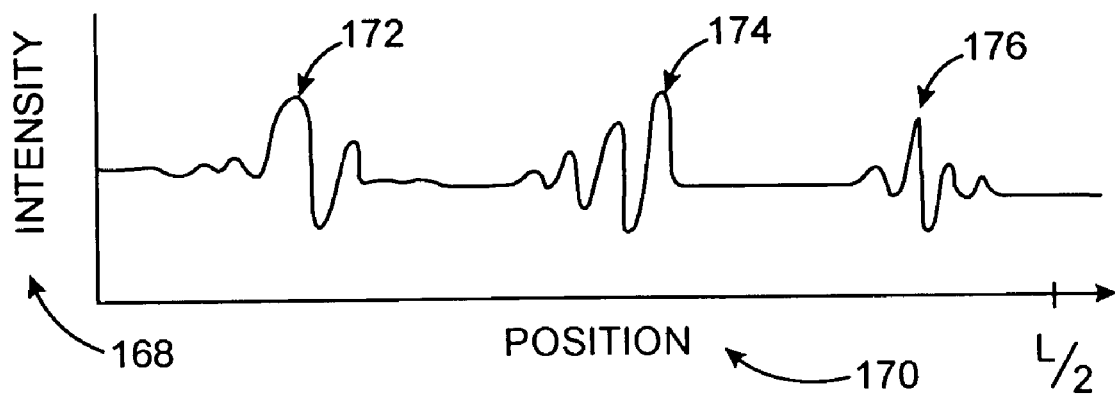
FIG. 10 illustrates measured reflected light intensities and positions along an optical path for a cornea after LASIK eye surgery, in accordance with an embodiment of the present invention.

An apparatus 100 calculates tissue tomography by combining spatial frequency components to determine a position and intensity of light reflected along an optical path as illustrated in FIG. 10. A band-limited inverse Fourier transform can be used to combine frequencies to determine an intensity and position of light reflected along an optical path. A plot of an intensity 168 of reflected light at a position 170 relative to a reference mirror 130 as described above is shown in FIG. 10. As illustrated, peaks of three reflecting surfaces are illustrated. A first peak 172 is located at a position indicating first reflecting surface of a cornea. A second peak 174 is located at a position indicating an interface between a LASIK flap and stromal bead. A third peak 176 is located at a position indicating a posterior surface of a cornea.

Figure 10A:
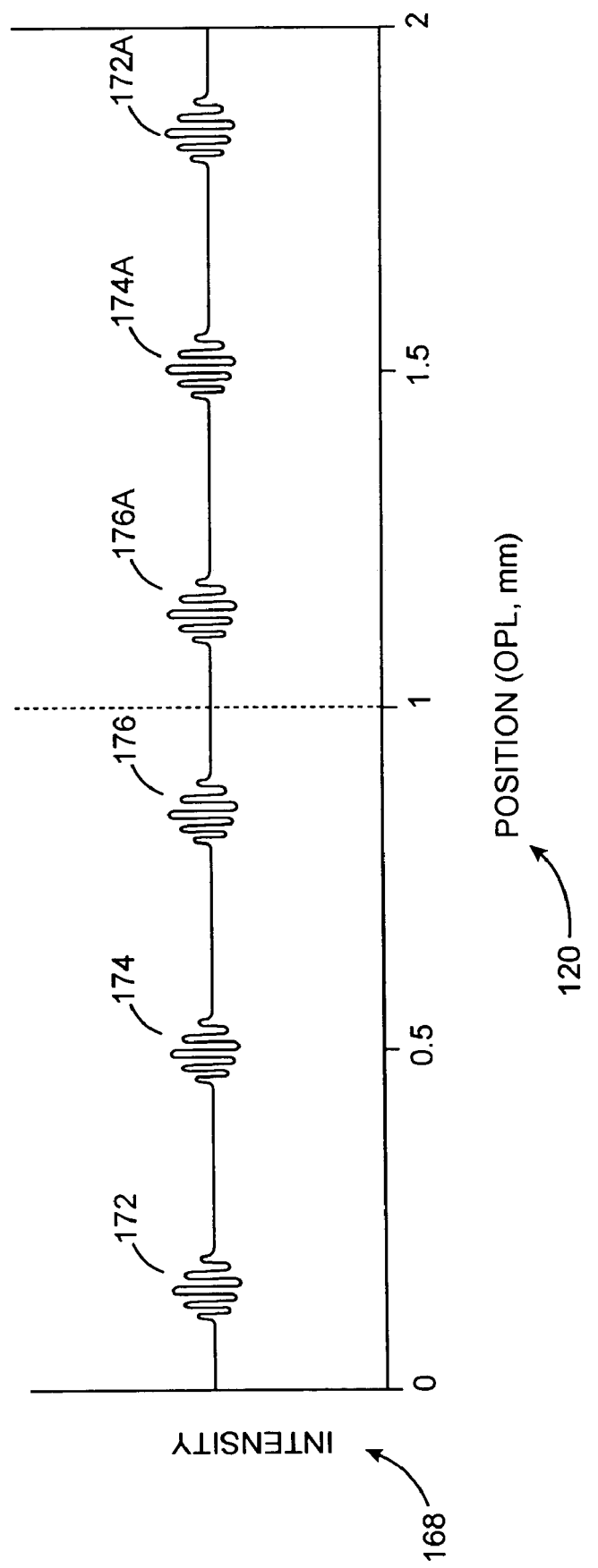
FIG. 10A illustrates phantom signals that may occur in an embodiment of the present invention.

In some embodiments, an inverse Fourier transform may result in phantom intensities of reflected light at phantom positions as illustrated in FIG. 10A. Phantom intensities having positions may arise from incomplete phase information of a measured interference signals. Phantom peaks 172A, 174A and 176A illustrate phantom intensities symmetrically positioned in relation to peaks 172, 174 and 176 along an optical path in relation to an etalon and a reference mirror. Phantom intensities and positions may be isolated so as not to interfere with actual tissue signals by controlling alignment of a tissue sample in relation to a reference mirror and a length of a tissue sample in relation to a length of an etalon. For example, a tissue sample may have an optical path length less than about half of an optical path length of an etalon, and a boundary of a measured surface may be positioned at an optical path length position nearly matching an optical path length of reference mirror as described above. A plot of intensities at positions may have an optical path length matching an optical path length of an etalon. For example an etalon may have an optical path length of 2 mm as illustrated in FIG. 10A. A dimension along a cornea is determined by dividing an optical path length by an index of refraction of a cornea.

By controlling a position of a cornea to be at a generally known location in relation to an etalon, phantom intensities at phantom positions may appear at locations removed from true corneal reflections and be excluded from tomographic measurements. As illustrated in FIG. 10A, phantom peaks 172A, 174A and 176A occur at locations removed from peaks 172, 174 and 176. As illustrated in FIG. 10A, a position is in relation to a reference mirror. By controlling a position of an anterior surface of a cornea 4 to be at an optical path length near a reference mirror and assuming that a distance through a cornea is less than about 1 mm of optical path length, phantom peaks 172A, 174A and 176A may be excluded from tomographic measurements.

Scanning a light beam across a cornea 4 and measuring interference signals at several locations across a cornea can make a three-dimensional tomography model of optical properties of a cornea 4. Several plots for each of several known locations are made as illustrated in FIG. 10. These plots of intensity are combined to make three dimensional tomography maps of corneal tissue.

In alternate embodiments, a controlled laser source emitting light at selected wavelengths of a Fourier series may be used as a light source. Several measurements may be sequentially taken at controlled wavelengths to generate interference signals for each of several wavelengths of a Fourier series. An interferometer having an optical path with a large cross section of several mm, for example a Twyman Green interferometer, may be used to generate two-dimensional interference signals on two dimensional area of a CCD array. Several optical fibers, each measuring a tomography along an optical path as described above, may be directed at a cornea. An interferometric topography apparatus measuring several points on a cornea with several optical fibers is described in U.S. Pat. No. 5,317,389, the full disclosure of which is incorporated herein by reference.

Optical Coherence Tomography

Figure 11:
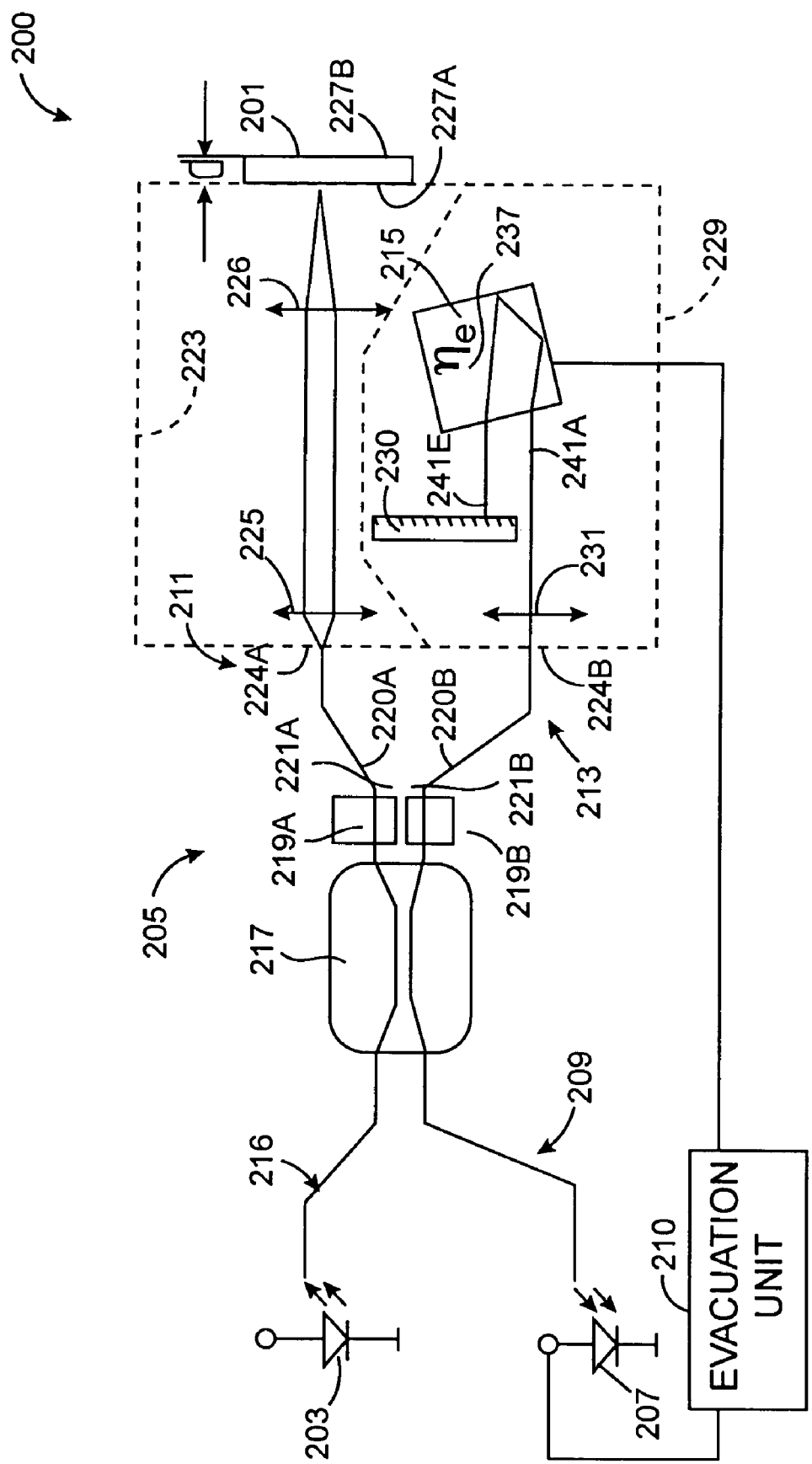
FIG. 11 is a schematic illustration of a tomographic system in accordance with an embodiment of the present invention.

FIG. 11 shows an optical coherence tomography ("OCT") apparatus 200 using a short coherence length light source for range measurements based on principles similar to white light interferometry. An OCT apparatus measures a pachymetry (thickness) of a cornea and may be scanned across a cornea to measure a tomography of a cornea. Systems and methods for measuring a tomography of a cornea are described in U.S. Pat. Nos. 6,004,314, 5,491,525 and 5,493,109, the full disclosures of which are incorporated herein by reference. FIG. 11 illustrates an embodiment of a system that may be integrated with a laser system 10 as described above. Many elements of tomography apparatus 200 are preferably included within light source module 9 as described above. An apparatus 200 includes a radiation source 203 with a short coherent length and a Michelson interferometer 205 for measuring a thickness d of an object 201 such as the cornea. A radiation source 203 may be a super-luminescent diode having a coherence length in a range of 10–15 μm.

An interferometer 205 includes a measuring branch 211, a reference branch 213, an illumination branch 216, and an observation branch 209, which are connected to one another by a 50/50% coupler 217. A radiation detector 207 and associated evaluation unit 210 are disposed within observation branch 209. A measured object 201 is arranged within measuring branch 211. Disposed just downstream of the coupler 217 is a polarization control unit 219A in the measuring branch 211 and another polarization control unit 219B in the reference branch 213. A radiation conductor 220A with detachable coupling 221A is connected to the polarization control unit 219a in the measuring branch 211, which leads to a measuring unit 223. A measuring unit 223 is also connected via a detachable coupling 224a to another end of the radiation conductor 220A. A measuring unit 223 has a lens 225 for collimating radiation passing through radiation conductor 220A. A focusing lens 226 focuses emitted radiation and collects radiation reflected from surfaces 227A, 227B of an object 201. A focusing lens 226 may be arranged so that radiation is focused at a back surface 227B having a very minimal degree of reflection in order to measure radiation reflected from a back surface 227B.

A radiation conductor 220B with detachable coupling 221b is also connected to a polarization control unit 219B of a reference branch 213, which leads to a reference unit 229 and a wavelength variator element 215, and a reflector 230 connected downstream thereof. Another end of a radiation conductor 220B is also connected via a detachable coupling 224b to a reference unit 229. In a reference unit 229, radiation that passed through a radiation conductor 220B is collimated through a lens 231 and beamed into a variator 215. Radiation is passed in the reference branch 213 and measuring branch 211 in such a way that the differences in dispersion in both branches 211, 213 can be disregarded, thereby preventing a dispersal of the interference signal.

A wavelength variator 215 has a refractive index $n_e$, and periodically changes an optical path length and wavelength of a beam in the reference branch 213 through natural rotation around a rotational axis 237. A cross-sectional area of a variator 215 on which a reference beam 241A of a reference branch 213 impinges is at least quadrilateral so that a reference beam path in a variator 215 is reflected at least twice at its inner surfaces. A reference beam 241E leaving a variator 215 can be reflected back, typically on itself, by a fixed reflector 230. In an embodiment, dimensions of side surfaces of the variator 215, a point of incidence of radiation thereon, and a refractive index of a variator material may be selected so that a wavelength difference achievable with rotation of variator 215 is approximately linear over an angle of rotation. Linearity provides a narrow bandwidth Doppler frequency shift to light emitted from a reference unit 220. A narrow bandwidth of a Doppler frequency shift permits good filtration, thereby producing a high signal-to-noise ratio measurement signal.

In a specific embodiment illustrated in FIG. 11, a coupler 217, polarization control units 219A, 219B, radiation source 203, radiation detector 207, reflector 230, lens 231, variator 215, and evaluation unit 210 are housed in a single device. A measuring unit 223 is linked via a radiation conductor 220A of an appropriate length to a remainder of apparatus 200, and is coupled to a scanning device 52 as described above for delivering a measurement beam to a cornea.

In many embodiments, an etalon 112 is positioned along an optical path of an illumination branch 216 of an interferometer as described above for selectively transmitting light as frequency and wavelength components of a Fourier series. Transmitted light is reflected from a cornea and combined as described above. Rotation of a variator 215 produces a Doppler shifted interference signal for each of several transmitted and reflected wavelengths. Alternatively, a reference mirror may be translated along an optical path. For example, reflector 230 may be movably mounted so as to translate along an optical path of reference beam 241e. Interference signals for each of several wavelengths of reflected light are measured from a signal comprising several interference signals. A measured interference signal for each of several wavelengths of reflected light is determined by taking a Fourier transform of a measured signal comprising several signals from several wavelengths of reflected light. Alternatively, a measured interference signal for each of several wavelengths of reflected light may be determined by least squares fitting of a measured interference signal. As transmitted and reflected wavelengths may be known based on properties of an etalon and a light source, least squares fitting to a measured signal may determine measured amplitudes and phases for each of several interference signals from a measured signal comprising several signals.

Physical dimensions and signals are illustrated for an embodiment in FIG. 11A. An etalon has an optical path length of 2 mm as described above, and a source emits light having a wavelength 302 centered near 800 nm and a spectral band of wavelengths with a full width half maximum of 32 nm. Along a 2 mm optical path length of an etalon 2500 frequency oscillations 304 of light having a wavelength 306 of 800 nm ($8 \times 10^{-7}$ m) will occur. A moving reference mirror has an optical path length velocity 308 of 1 meter per second (twice a velocity of a reference mirror) and produces a central Doppler shifted interference signal at a temporal frequency 310 of 1.25 MHz ($1.25 \times 10^6$ cycles/s) and a spatial frequency 312 of $1.25 \times 10^6$ cycles per meter for a central wavelength of 800 nm. Additional wavelengths of light emitted by a light source are transmitted by an etalon and reflected from a cornea as described above. A wavelength 306 of additional frequencies of transmitted and reflected light are determined by a number of oscillations 304. A difference in wavelength 314 illustrates a spectral line width among transmitted wavelengths of light. A Doppler frequency (Hz) 315 illustrates a frequency at which each spectral component is measured at a detector 207. A difference in Doppler frequency 316 illustrates sideband frequencies at 500 Hz intervals about a central frequency of 1.25 MHz. A spatial frequency 318 in cycles per mm illustrates spatial frequencies of each wavelength of transmitted and reflected light. A difference in spatial frequency 320 illustrates a difference in spatial frequency between adjacent wavelengths of light.

Each interference signal may be measured with a composite signal from a single detector 207 with a measured energy detector signal data acquisition rate of at least 5 MHz and a spatial sampling density of at least about 5000 measured energy detector signal data samples per mm. A Fourier transform of such a measured composite signal may determine a measured interference signal for each of several wavelengths of reflected light.

Figure 11B:
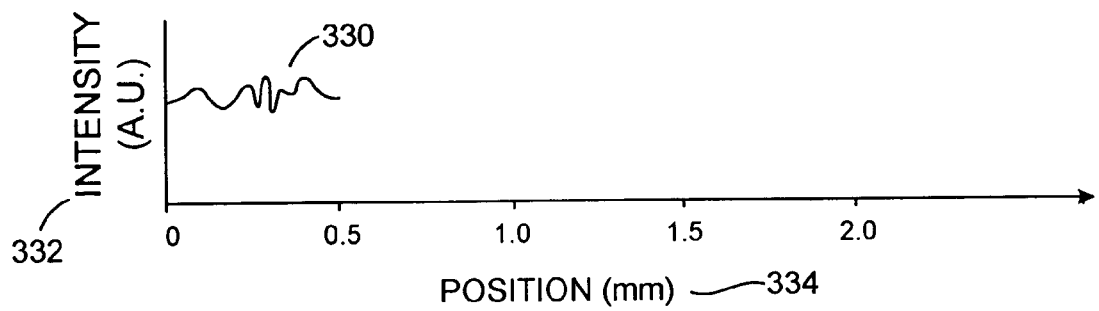

FIG. 11B illustrates a composite signal 330 of an intensity 332 at a position 334 of a moving reference mirror as described above. In some embodiments, a mirror may not move an optical path length by an entire length of an etalon. For example, a mirror may move 0.25 mm to vary an optical path by 0.5 mm for an Etalon having a length of 2 mm. A signal may be padded with any arbitrary value, for example 0, to complete a data set in preparation for Fourier spectral analysis. A measurement data sampling frequency may be an integer multiple of Fourier frequencies passed by an etalon. For example, for 2500 oscillations along a 2 mm optical path, spatial frequencies of 1250 cycles per mm are present, and a data sampling frequency may be 5000 cycles per mm and four times a transmitted optical signal spatial frequency. For a measurement having 1250 samples over a 0.5 mm length and an etalon having an optical path length of 2.0 mm as illustrated in FIG. 11B, a data set may be padded with a value of zero for 3750 values from 0.5 mm to 2.0 mm. Alternatively, least squares regression may be used to fit a data set of 1250 samples over a 0.5 mm length with known frequency components produced by an etalon with an optical path of 2.0 mm so as to determine an amplitude and a phase of reflected frequency components.

Figure 11C:
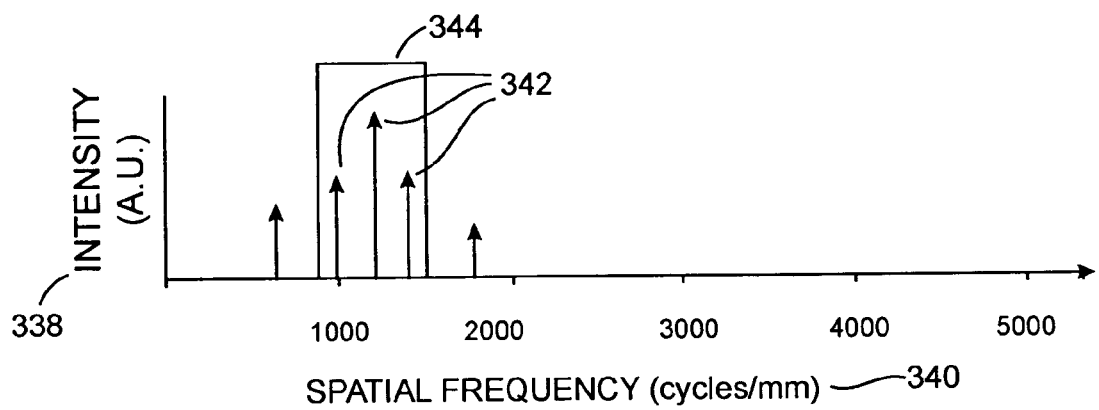

FIG. 11C illustrates measured interference signals for each of several wavelengths as determined by a Fourier transform. An intensity 338 is shown at a spatial frequency 340 for each of several measured interference signals 342 of light reflected from a cornea. Each interference signal may be a complex number. As the frequencies of reflected light are known, a digital filter in the form of a window 344 may selectively pass measured frequencies matching frequencies of light emitted by a source and transmitted by an etalon. For example, FIG. 11A illustrates a spatial frequency 318 for each wavelength to be near 1250 cycles per mm.

Figure 11D:
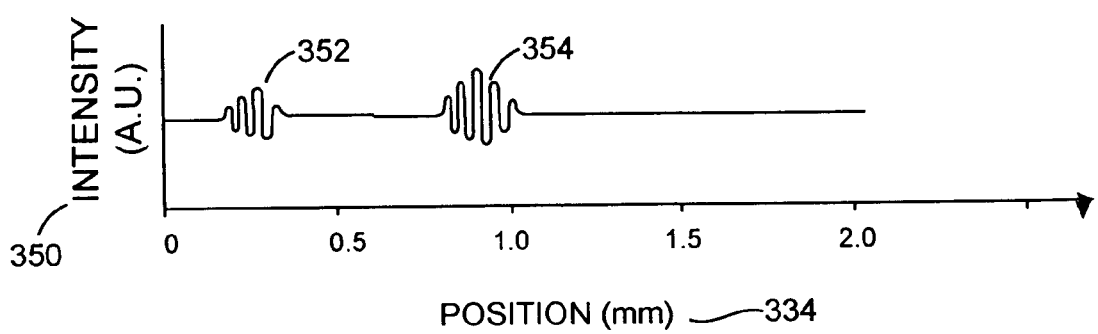

FIG. 11D illustrates positions of reflecting surfaces determined by combining measured interference signals. An intensity 350 of reflected light in arbitrary units is shown at a position 334 for each of several positions. A first peak 352 and a second peak 354 are illustrated. A first peak 352 is located at a position of a reflecting anterior surface of a cornea, and a second peak 354 is located at a position of a reflecting posterior surface of a cornea. Positions of other reflecting surfaces and tissues of a cornea may be determined. For example, an entire optical path of an eye may be measured from a cornea to a retina. Also, optical properties such a tissue scattering may be measured.

Optical properties of a tissue may be determined over a distance along an optical path by varying an optical path length of a reference mirror only a fraction a distance along an optical path. As illustrated with reference to FIGS. 11A–11D, optical properties may be determined along a 2 mm distance of an optical path by moving a mirror ½ mm. An entire optical path of an eye having a distance of about 30 mm may be measured by moving a mirror a distance of about 1 mm and less. A distance a mirror is moved is related to a bandwidth and spatial frequencies of reflected light components.

An inverse Fourier transform of several measured interference signals combines several interference signals and determines an intensity of reflected light along an optical path. An inverse transform may be limited to have spatial frequencies within a window of a filter as described above. A Fourier transform of a limited band of frequencies may be referred to as a band limited Fourier transform. A band limited transform may exhibit oscillations around a peak in reflected intensity as illustrated near first peak 352 and second peak 354 of FIG. 11D.

Figure 12:
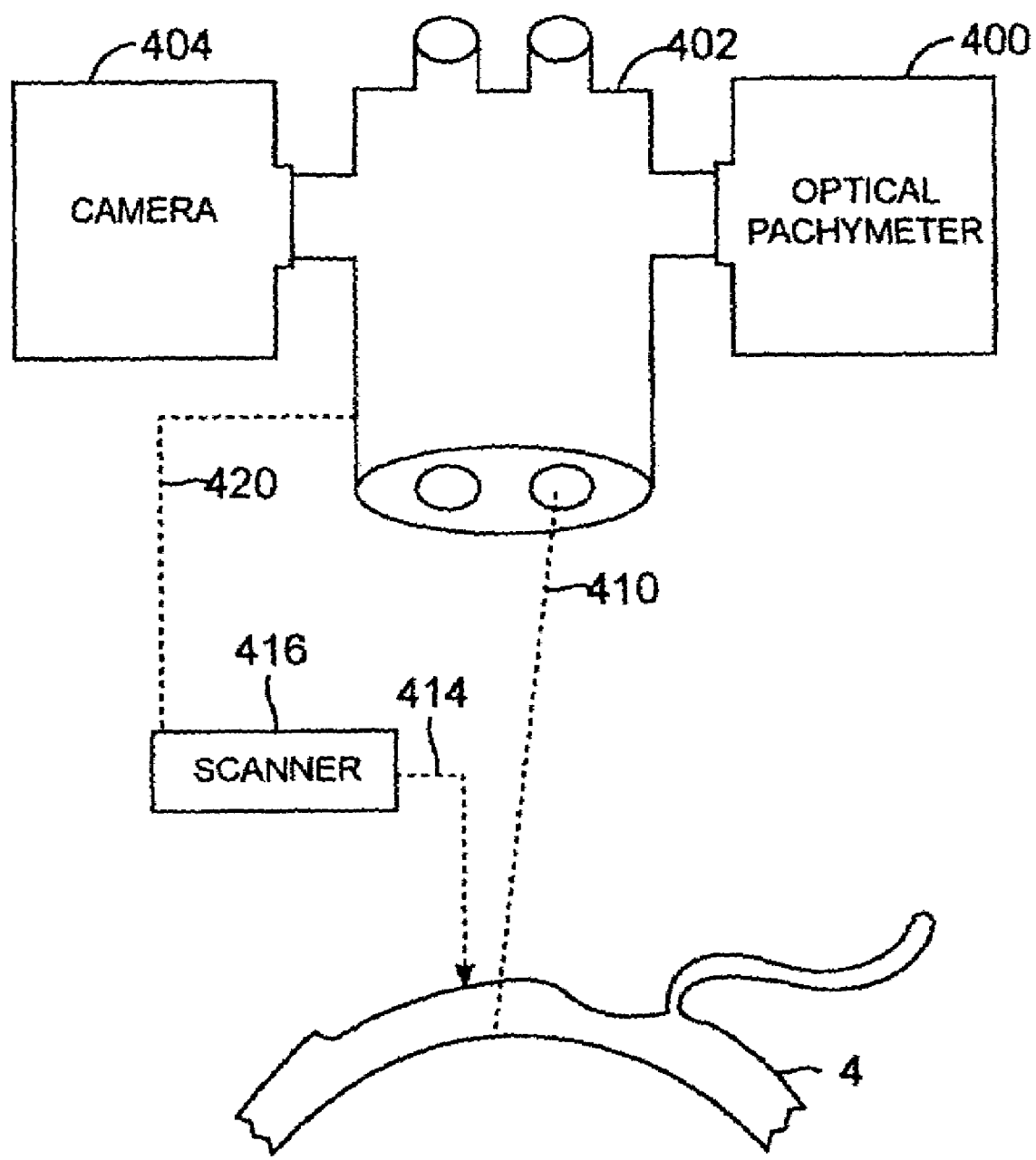
FIG. 12 is a schematic diagram illustrating integration a tomography system with an operating microscope in accordance with an embodiment of the invention.

FIG. 12 shows an embodiment integrating an optical pachymeter as described above with a microscope 402 of a system as described above. The microscope 402 has one viewing port coupled to a camera 404, and another viewing port coupled to a pachymeter 400. Microscope 402 may be a laser vision correction operating microscope commonly used in surgery, and provides a convenient coupling site for integrating a pachymeter 400.

A measurement beam 410 generated by a optical pachymeter 400 is directed to a cornea via a microscope 402 in a slightly off-axis manner. An off-axis measurement can be compensated for by a correction factor determined from geometric dimensions of the apparatus, and an off axis beam may be directed slightly away from an apex of a cornea to provide an increased amount of light reflected back into a microscope 402. FIG. 12 illustrates an ablative beam 414 delivered by a beam delivery device such as a scanner 416 to a cornea 4. In a specific embodiment, a scanner 416 and a camera 402 are coupled together as indicated by electrical communication 420 to move synchronously. A system controller similar to a processor 22 of FIG. 1 may be in electrical communication with a scanner 416, a microscope 402, and a pachymeter 400 for controlling their operations.

It is to be understood that the above description is intended to be illustrative and not restrictive. Many embodiments will be apparent to those of skill in the art upon reviewing the above description. For instance, an arrangement of optical elements for delivering ablative and measurement beams may be modified. Alternate tomography measurement devices may be integrated with an ablative system. While specific reference has been made to an etalon and a Fourier transform, optical wavelengths may be selected by other means and other transforms may be used. Therefore, the scope of the invention should be determined not with reference to the above description, but instead should be determined with reference to the appended claims along with full scope of their equivalents.

What is claimed is:

1. A method of measuiring a thickness of a tissue, the method comprising:
   directing a measurement light beam along an optical path toward the tissue;
   providing a structure along the optical path;
   selecting three wavelengths of corresponding with wavelengths of a Fourier series with the structure;
   reflecting the three wavelengths of light from the tissue;
   measuring an interference signal for each of the three wavelengths of to reflected light; and
   determining a separation distance between positions of at least two reflecting tissue surfaces along to optical path by combining the measured interference signals.

2. The method of claim 1 further comprising:
   determining an intensity of the reflected light bean several positions along the optical path combining the measured interferencnignals; and
   wherein to measurement light beam comprises the three wavelengths of light simultaneously directed along the path toward the tissue, and wherein the three interference signals are measured simultaneously.

3. The method of claim 1 wherein the Fourier series corresponds to a distance along the optical path and each of the three wavelengths of light undergoes an integer number of oscillations over the distance along the optical path.

4. The method of claim 3 further comprising:
   transforming the measured interference signal to spatial position components by taking an inverse Fourier transform using the measured interference signals, the spatial position components describing positions and intensities of the light beam reflected from the tissue along the optical path.

5. The method of claim 1 further comprising determining a tomography of the tissue by directing the measurement beam to several locations of the tissue, the locations having at least two reflecting tissue surfaces along the optical path.

6. The method of claim 5 further comprising:
   scanning the light beam from a first location to a second location, wherein the first location and the second location are among the locations used to determine the tomography of the tissue.

7. A method of treating a tissue, the method comprising:
   directing an ablative light beam to the tissue to form a desired shape in the tissue;
   providing a structure along an optical path; selecting three wavelengths of light to correspond with wavelengths of a Fourier series with the structure;
   reflecting the three wavelengths of light from the tissue by directing a measurement light beam along the optical path toward the tissue;
   measuring an interference signal for each of the three wavelengths of the reflected light; and
   determining positions of at least two reflecting tissue surfaces along the optical path by combining the measured signals while the ablative light beam is directed toward the tissue.

8. The method of claim 7 further comprising:
   determining intensity of the reflected light beam at several position along the optical path; and
   wherein the measurement light beam comprises the three wavelengths of light simultaneously directed along the path toward the tissue and wherein the three interference signals are measured simultaneously.

9. The method of claim 7 whrein the Fourier series corresponds to distance along the optical path, and each of the three wavelengths of light undergoes an integer number of oscillations over the distance along the optical path.

10. The method of claim 9 further comprising:
    transforming the measured interference siqnals to spatial position components by taking an inverse Fourier transform using the measured interference signals, the spatial position components describing positions and intensities of the light beam reflected from the tissue along the optical path.

11. A system for measuring a thickness of a tissue, the system comprising;
    a light source emitting a measurement light beam, the measurement light beam directed along an optical path toward the tissue, three wavelengths of the light beam reflecting from the tissue;
    a structure disposed along the optical path, the structure selecting the three wavelengths of light to correspond with wavelengths of a Fourier Series;
    an interferometer generating an interference signal for each of the three wavelengths of the measurement light beam reflected from the tissue; and
    a processor determining a separation distance between positions of at least two reflecting tissue surfaces along the optical path by combining the measured interference signals.

12. The system of claim 11 wherein:
    the processor determines intensity of the reflected light beam several positions alone the optical path;
    the measurement light beam comprises the three wavelengths of light simultaneously directed along the path toward the tissue; and
    the three interference signals are measured simultaneously.

13. The system of claim 11 wherein the Fourier series corresponds to a distance along the optical path and each of the three wavelengths of light undergoes an integer number of oscillations over the distance.

14. The system of claim 13 wherein the processor transforms the measured interference signals to spatial position components with an inverse Fourier transform using the measured interference signals, the spatial position components describing positions and intensities of the light beam reflected from the tissue along the optical path.

15. The system of claim 14 further comprising an optical system directing the measurement beam to several locations of the tissue so as to determine a tomography of the tissue, the locations having at least two reflecting tissue surfaces along the optical path.

16. The system of claim 15 further comprising:
    wherein the optical system scans the light beam from a first location to a second location, and wherein the first location and the second location are among the locations used to determine the tomography of the tissue.

17. A system far treating a tissue, the system comprising:
    an ablative fight source emitting an ablative light beam;

a light source emitting a measurement light beam, the measurement light beam directed along an optical path toward the tissue, three wavelengths of the light beam reflecting from the tissue;

a structure disposed along the optical path to select the three wavelengths of light to correspond with wavelengths of a Fourier Series;

an interferometer generating an interference signal for each of the three wavelengths of the measurement light beam reflected from the tissue; and a processor controlling the ablative light beam and determining positions of at least two reflecting tissue surfaces along the optical path by combining the measured interference signals.

18. The system of claim 17 wherein;
the processor determines an intensity of the reflected light beam at several positions along the optical path;
the measurement light beam comprises the three wavelengths of light simultaneously directed along the path toward the tissue; and
the three interference signals are measured simultaneously.

19. The system of claim 17 wherein:
the Fourler series corresponds to a distance along the optical path and each of the three wavelengths undergoes an integer number of oscillations over the distance; and
the processor transforms the measured inerferrence signals to spatial position components with an inverse Fourier transform using the measured interference signals the spatial position components describing positions and intensities of the light beam reflected from the tissue along the optical path.

20. An apparatus for treating tissue comprising:
a ablative light source producing an ablative beam;
a beam delivery device directing the ablative beam onto a tissue;
a microscope having a viewing port; and
an optical pachymeter emitting a measurement light beam directed along an optical path toward the tissue, three wavelengths of the light beam reflecting from the tissue;
a structure disposed along the optical path to select the three wavelengths of light to correspond with wavelengths of a Fourier series;
an interferometer generating an interference signal for each of the three wavelengths of the measurement light beam reflected from the tissue; and
a processor determining a separation distance between positions of at least two reflecting tissue surfaces along the optical path by combining the measured interference signals.

21. The ablation apparatus of claim 20 wherein:
the processor determines an intensity of the reflected light beam at several positions along the optical path;
the measurement light beam comprises the three wavelengths of light simultaneously directed along the path toward the tissue; and
the three interference signals are measured simultaneously.

22. The ablation apparatus of claim 20 wherein the Fourier series corresponds to a distance along the optical path and each wavelength of light undergoes an integer number of oscillations over the distance, and wherein the processor transforms the measured interference signals to spatial position components with an inverse Fourier transform using the measured interference signals, the spatial position components describing positions and intensities of the light beam reflected from the tissue along the optical path.

23. A method of measuring a separation distance between positions of at least two reflections along an optical path, the method comprising;
reflecting at least three wavelengths of light from the positions by directing a measurement light beam along the optical path;
selecting the three wavelengths of light to correspond with wavelengths of a Fourier series by providing a structure along the optical path, the structure selecting the wavelengths of light;
measuring an interference signal for each of the three wavelengths of the reflected light; and
determining the separation distance between the positions of the at least two reflections along the optical path by combining the measured interference signals.

24. A method of measuring a thickness of a tissue, the method comprising:
reflecting ten wavelengths of light from the tissue by directing a measurement light beem along an optical path toward the tissue;
providing a structure along the optical path;
selectig the ten wavelengths of light to correspond with wavelengths of a Fourier series with the structure;
measuring an interference signal for each of the ten wavelengths of the reflected light; and
determining a separation distance between positions of at least two reflecting tissue surfaces along the optical path by combining the measured interference signals.

25. The method of claim 24 further comprising:
determining an intensity of the reflected light beam at several positions along the optical path by combining the measured interference signals; and
wherein the measurement light beam comprises the ten wavelengths off light simultaneously directed along the path toward the tissue, and wherein the ten interference signals are measured simultaneously.

26. The method of claim 24 wherein the Fourier series corresponds to a distance along the optical path, and each of the ten wavelengths of light undergoes an integer number of oscillations over the distance along the optical path.

27. The method of claIm 26 further comprising:
transforming the measured interference signal to spatial position components by taking an inverse Fourier transform using the measured interference signals, the spatial position components describing positions and intensities of the light beam reflected from the tissue along the optical path.

* * * * *

UNITED STATES PATENT AND TRADEMARK OFFICE
CERTIFICATE OF CORRECTION

PATENT NO.       : 7,133,137 B2
APPLICATION NO.  : 10/601119
DATED            : November 7, 2006
INVENTOR(S)      : John K. Shimmick It is certified that error appears in the above-identified patent and that said Letters Patent is hereby corrected as shown below:

Column 17, Claim 1, Line 17 – The word "light" should be inserted between "of" and "corresponding"

Column 17, Claim 1, Line 21 – The word "to" should be changed to --the--

Column 17, Claim 1, Line 23 – The word "to" should be changed to --the--

Column 17, Claim 2, Line 27 – The word "by" should be inserted between "path" and "combining"

Column 17, Claim 2, Line 28 – The word "interferencnignals" should be changed to --interference signals--

Column 17, Claim 4, Line 38 – The word "signal" should be changed to --signals--

Column 18, Claim 8, Line 2 – The word "an" should be inserted between "determining" and "intensity"

Column 18, Claim 8, Line 3 – The word "position" should be changed to --positions--

Column 18, Claim 9, Line 8 – The word "whrein" should be changed to --wherein--

Column 18, Claim 9, Line 9 – The word "a" should be inserted between "to" and "distance"

Column 18, Claim 12, Line 37 – The word "an" should be inserted between "determines" and "intensity"

Column 18, Claim 12, Line 38 – The word "at" should be inserted between "beam" and "several"

UNITED STATES PATENT AND TRADEMARK OFFICE
CERTIFICATE OF CORRECTION

PATENT NO. : 7,133,137 B2
APPLICATION NO. : 10/601119
DATED : November 7, 2006
INVENTOR(S) : John K. Shimmick It is certified that error appears in the above-identified patent and that said Letters Patent is hereby corrected as shown below:

Column 19, Claim 19, Line 32 – A comma should be inserted after "nals"

Signed and Sealed this

Thirtieth Day of January, 2007

JON W. DUDAS
*Director of the United States Patent and Trademark Office*